United States Patent [19]

Jarsch

[11] Patent Number: 5,916,759
[45] Date of Patent: Jun. 29, 1999

[54] **CHOLESTEROL OXIDASE FROM *BREVIBACTERIUM STEROLICUM***

[75] Inventor: Michael Jarsch, Bad Heilbrunn, Germany

[73] Assignee: Boehringer Mannheim GmbH, Mannheim, Germany

[21] Appl. No.: 08/532,795

[22] PCT Filed: May 2, 1994

[86] PCT No.: PCT/EP94/01394

§ 371 Date: Jan. 5, 1996

§ 102(e) Date: Jan. 5, 1996

[87] PCT Pub. No.: WO94/25603

PCT Pub. Date: Nov. 10, 1994

[30] Foreign Application Priority Data

May 5, 1993 [DE] Germany .............................. 43 14 793
Dec. 9, 1993 [DE] Germany .............................. 43 42 012

[51] Int. Cl.$^6$ ................................ C12Q 1/60; C12Q 1/26; C12N 9/04; C12N 15/53

[52] U.S. Cl. ................................ 435/11; 435/25; 435/190; 536/23.2

[58] Field of Search .................................. 435/190, 11, 25; 536/23.2

[56] References Cited

U.S. PATENT DOCUMENTS 4,374,930  2/1983  Snoke et al. .............................. 435/190
5,602,017  2/1997  Fujishiro et al. ....................... 435/190

FOREIGN PATENT DOCUMENTS 452112  10/1991  European Pat. Off. .

OTHER PUBLICATIONS

Ohta et al., Biosci. Biotech. Biochem. 56:1786–1791, 1992.
Ohta et al., Gene 103:93–96, 1991.

*Primary Examiner*—Charles L. Patterson, Jr.
*Attorney, Agent, or Firm*—Nikaido Marmelstein Murray & Oram, LLP

[57] ABSTRACT

The invention concerns a cholesterol oxidase, a process for the production of a recombinant cholesterol oxidase, a DNA sequence suitable for this process which causes a cytoplasmatic expression of the recombinant cholesterol oxidase in a host bacterium as well as the recombinant cholesterol oxidase obtianed in this way.

12 Claims, 4 Drawing Sheets

Figur 1
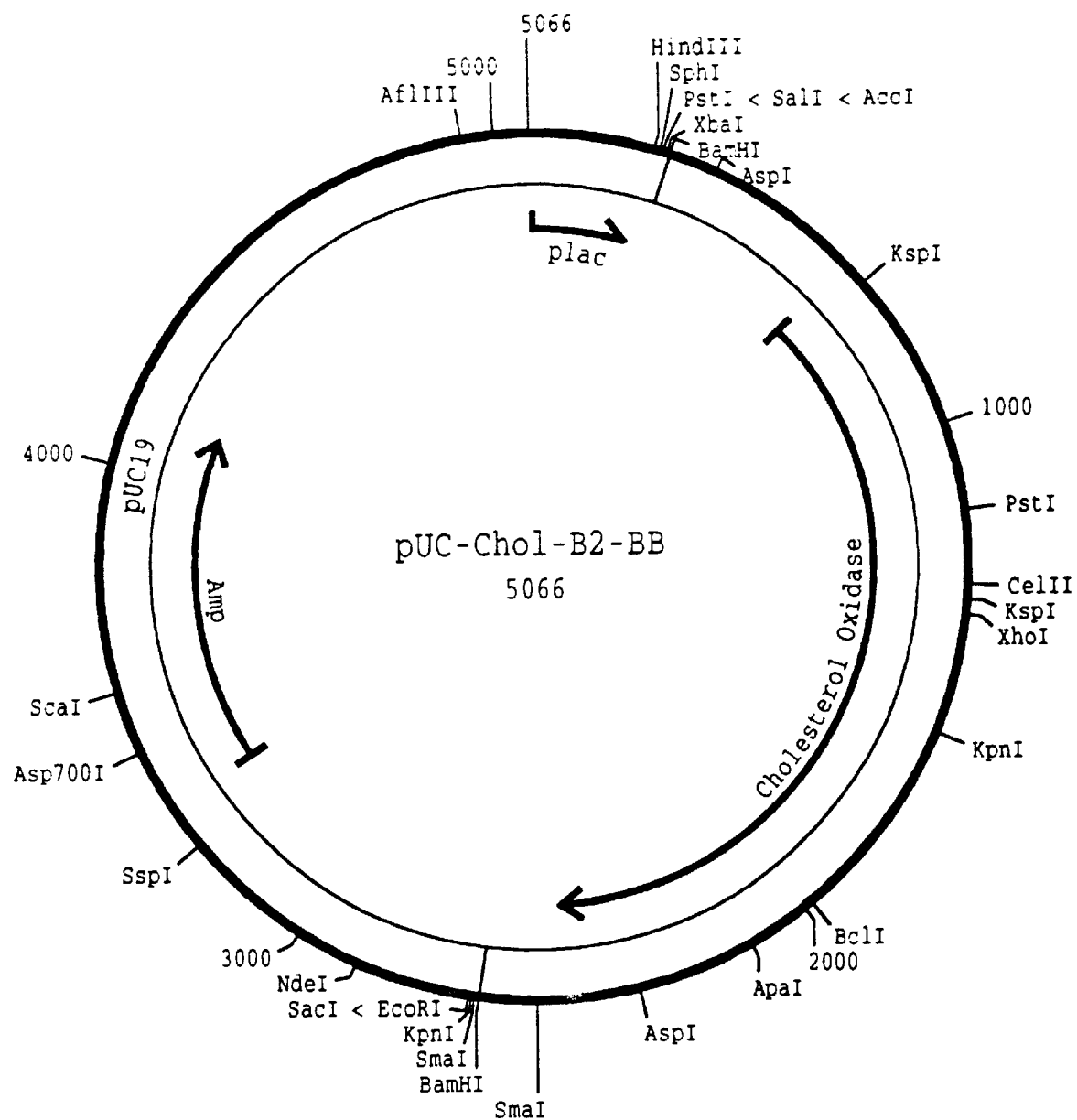

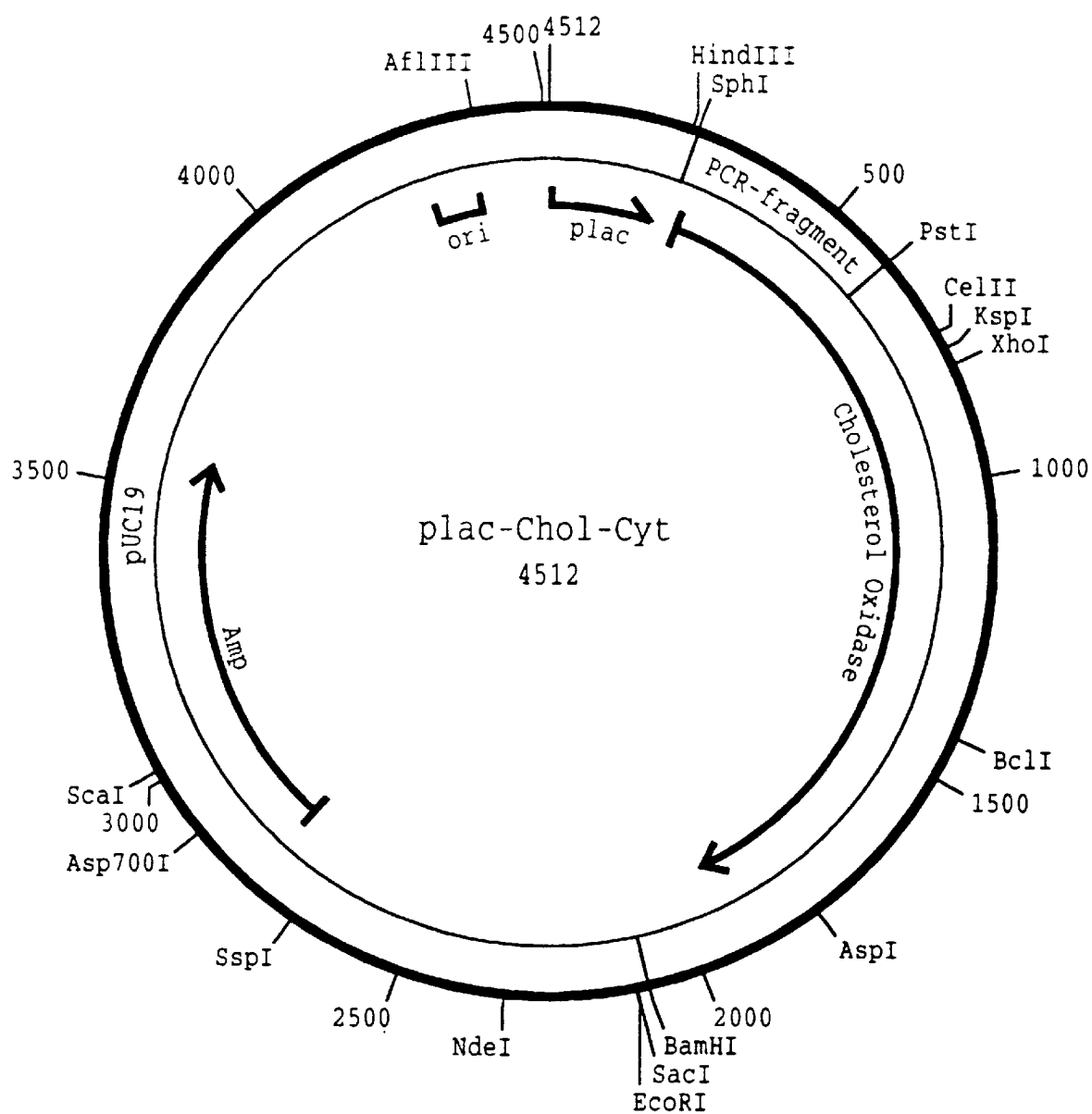
Figur 2

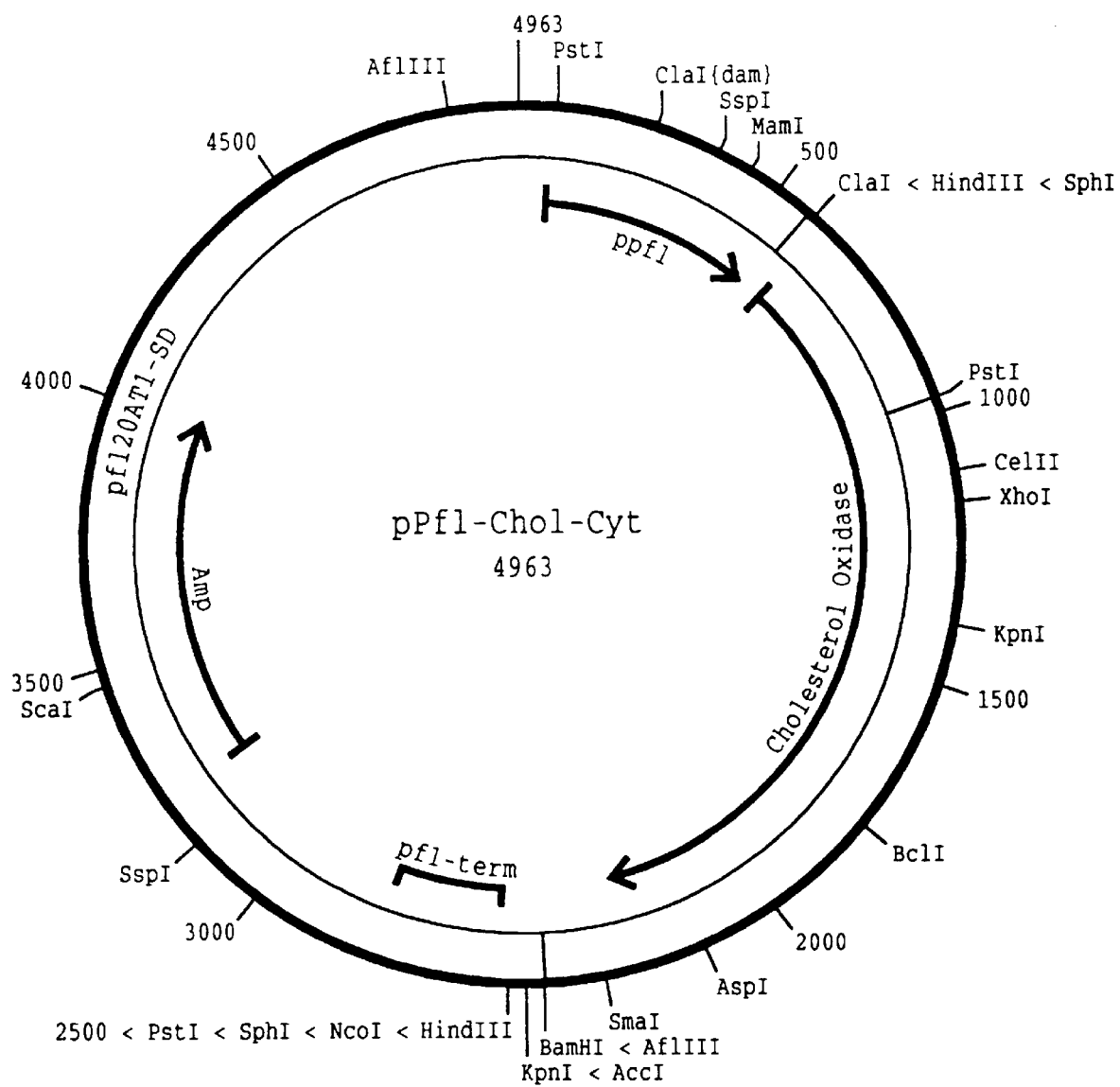
Figur 3

Figur 4
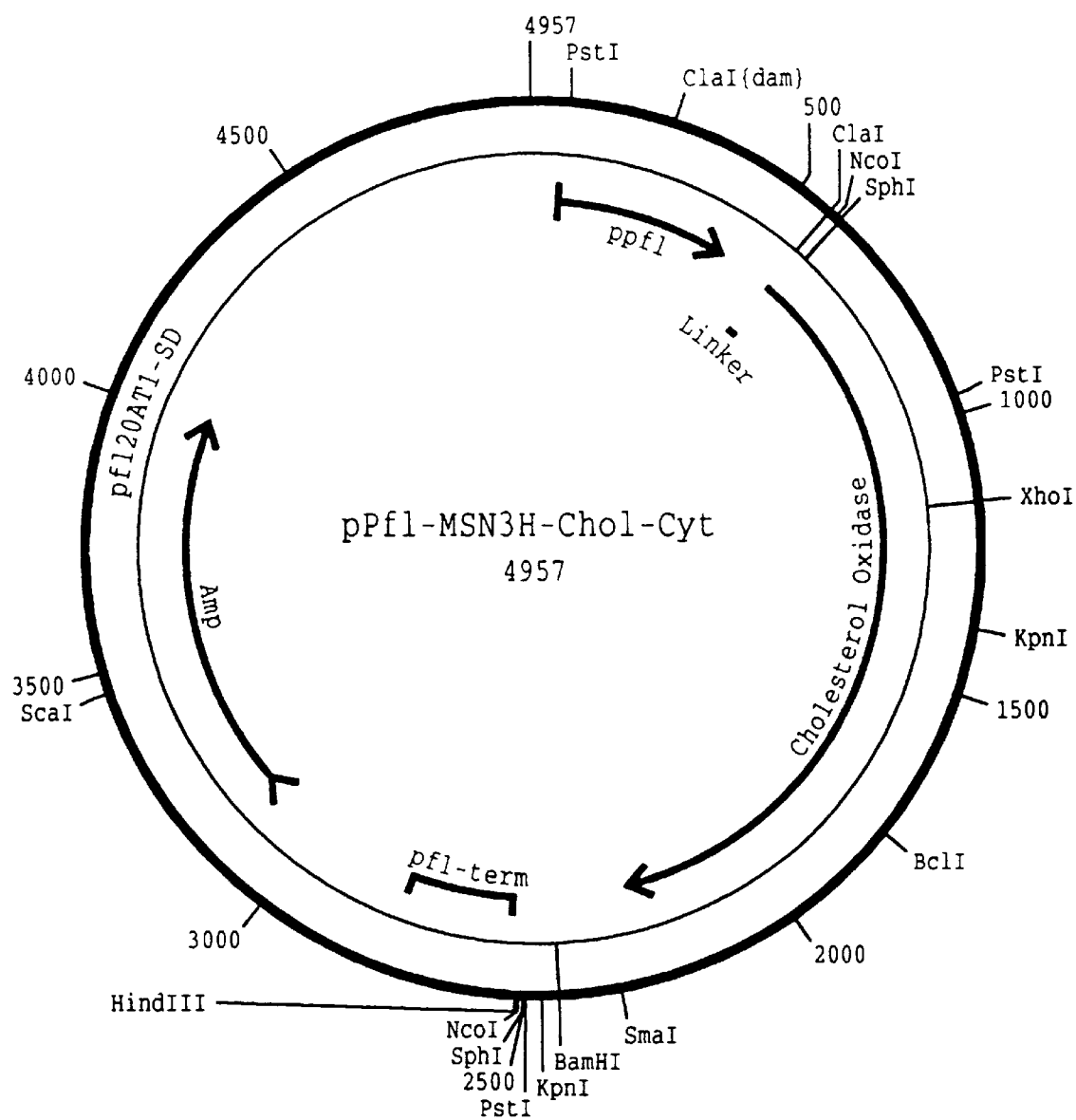

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 1683 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..1683

(xi) SEQUENCE DESCRIPTION: SEQ ID NO:1:

```
TCG ACC GGG CCG GTC GCG CCG CTT CCG ACG CCG CCG AAC TTC CCG AAC       48
Ser Thr Gly Pro Val Ala Pro Leu Pro Thr Pro Pro Asn Phe Pro Asn
 1               5                  10                  15

GAC ATC GCG CTG TTC CAG CAG GCG TAC CAG AAC TGG TCC AAG GAG ATC       96
Asp Ile Ala Leu Phe Gln Gln Ala Tyr Gln Asn Trp Ser Lys Glu Ile
             20                  25                  30

ATG CTG GAC GCC ACT TGG GTC TGC TCG CCC AAG ACG CCG CAG GAT GTC      144
Met Leu Asp Ala Thr Trp Val Cys Ser Pro Lys Thr Pro Gln Asp Val
         35                  40                  45

GTT CGC CTT GCC AAC TGG GCG CAC GAG CAC GAC TAC AAG ATC CGC CCG      192
Val Arg Leu Ala Asn Trp Ala His Glu His Asp Tyr Lys Ile Arg Pro
     50                  55                  60

CGC GGC GCG ATG CAC GGC TGG ACC CCG CTC ACC GTG GAG AAG GGG GCC      240
Arg Gly Ala Met His Gly Trp Thr Pro Leu Thr Val Glu Lys Gly Ala
 65                  70                  75                  80

AAC GTC GAG AAG GTG ATC CTC GCC GAC ACG ATG ACG CAT CTG AAC GGC      288
Asn Val Glu Lys Val Ile Leu Ala Asp Thr Met Thr His Leu Asn Gly
                 85                  90                  95

ATC ACG GTG AAC ACG GGC GGC CCC GTG GCT ACC GTC ACC GCC GGT GCC      336
Ile Thr Val Asn Thr Gly Gly Pro Val Ala Thr Val Thr Ala Gly Ala
            100                 105                 110

GGC GCC AGC ATC GAG GCG ATC GTC ACC GAA CTG CAG AAG CAC GAC CTC      384
Gly Ala Ser Ile Glu Ala Ile Val Thr Glu Leu Gln Lys His Asp Leu
        115                 120                 125

GGC TGG GCC AAC CTG CCC GCT CCG GGT GTG CTG TCG ATC GGT GGC GCC      432
Gly Trp Ala Asn Leu Pro Ala Pro Gly Val Leu Ser Ile Gly Gly Ala
    130                 135                 140

CTT GCG GTC AAC GCG CAC GGT GCG GCG CTG CCG GCC GTC GGC CAG ACC      480
Leu Ala Val Asn Ala His Gly Ala Ala Leu Pro Ala Val Gly Gln Thr
145                 150                 155                 160

ACG CTG CCC GGT CAC ACC TAC GGT TCG CTG AGC AAC CTG GTC ACC GAG      528
Thr Leu Pro Gly His Thr Tyr Gly Ser Leu Ser Asn Leu Val Thr Glu
                165                 170                 175

CTG ACC GCG GTC GTC TGG AAC GGC ACC ACC TAC GCA CTC GAG ACG TAC      576
Leu Thr Ala Val Val Trp Asn Gly Thr Thr Tyr Ala Leu Glu Thr Tyr
            180                 185                 190

CAG CGC AAC GAT CCT CGG ATC ACC CCA CTG CTC ACC AAC CTC GGG CGC      624
Gln Arg Asn Asp Pro Arg Ile Thr Pro Leu Leu Thr Asn Leu Gly Arg
        195                 200                 205

TGC TTC CTG ACC TCG GTG ACG ATG CAG GCC GGC CCC AAC TTC CGT CAG      672
Cys Phe Leu Thr Ser Val Thr Met Gln Ala Gly Pro Asn Phe Arg Gln
    210                 215                 220

CGG TGC CAG AGC TAC ACC GAC ATC CCG TGG CGG GAA CTG TTC GCG CCG      720
Arg Cys Gln Ser Tyr Thr Asp Ile Pro Trp Arg Glu Leu Phe Ala Pro
```

-continued

| | |
|---|---|
| AAG GGC GCC GAC GGC CGC ACG TTC GAG AAG TTC GTC GCG GAA TCG GGC<br>Lys Gly Ala Asp Gly Arg Thr Phe Glu Lys Phe Val Ala Glu Ser Gly<br>245                      250                      255 | 768 |
| GGC GCC GAG GCG ATC TGG TAC CCG TTC ACC GAG AAG CCG TGG ATG AAG<br>Gly Ala Glu Ala Ile Trp Tyr Pro Phe Thr Glu Lys Pro Trp Met Lys<br>260                      265                      270 | 816 |
| GTG TGG ACG GTC TCG CCG ACC AAG CCG GAC TCG TCG AAC GAG GTC GGA<br>Val Trp Thr Val Ser Pro Thr Lys Pro Asp Ser Ser Asn Glu Val Gly<br>275                      280                      285 | 864 |
| AGC CTC GGC TCG GCG GGC TCC CTC GTC GGC AAG CCT CCG CAG GCG CGT<br>Ser Leu Gly Ser Ala Gly Ser Leu Val Gly Lys Pro Pro Gln Ala Arg<br>290                      295                      300 | 912 |
| GAG GTC TCC GGC CCG TAC AAC TAC ATC TTC TCC GAC AAC CTG CCG GAG<br>Glu Val Ser Gly Pro Tyr Asn Tyr Ile Phe Ser Asp Asn Leu Pro Glu<br>305                      310                      315                      320 | 960 |
| CCC ATC ACC GAC ATG ATC GGC GCC ATC AAC GCC GGA AAC CCC GGA ATC<br>Pro Ile Thr Asp Met Ile Gly Ala Ile Asn Ala Gly Asn Pro Gly Ile<br>325                      330                      335 | 1008 |
| GCA CCG CTG TTC GGC CCG GCG ATG TAC GAG ATC ACC AAG CTC GGG CTG<br>Ala Pro Leu Phe Gly Pro Ala Met Tyr Glu Ile Thr Lys Leu Gly Leu<br>340                      345                      350 | 1056 |
| GCC GCG ACG AAT GCC AAC GAC ATC TGG GGC TGG TCG AAG GAC GTC CAG<br>Ala Ala Thr Asn Ala Asn Asp Ile Trp Gly Trp Ser Lys Asp Val Gln<br>355                      360                      365 | 1104 |
| TTC TAC ATC AAG GCC ACG ACG TTG CGA CTC ACC GAG GGC GGC GGC GCC<br>Phe Tyr Ile Lys Ala Thr Thr Leu Arg Leu Thr Glu Gly Gly Gly Ala<br>370                      375                      380 | 1152 |
| GTC GTC ACG AGC CGC GCC AAC ATC GCG ACC GTG ATC AAC GAC TTC ACC<br>Val Val Thr Ser Arg Ala Asn Ile Ala Thr Val Ile Asn Asp Phe Thr<br>385                      390                      395                      400 | 1200 |
| GAG TGG TTC CAC GAG CGC ATC GAG TTC TAC CGC GCG AAG GGC GAG TTC<br>Glu Trp Phe His Glu Arg Ile Glu Phe Tyr Arg Ala Lys Gly Glu Phe<br>405                      410                      415 | 1248 |
| CCG CTC AAC GGT CCG GTC GAG ATC CGC TGC TGC GGG CTC GAT CAG GCA<br>Pro Leu Asn Gly Pro Val Glu Ile Arg Cys Cys Gly Leu Asp Gln Ala<br>420                      425                      430 | 1296 |
| GCC GAC GTC AAG GTG CCG TCG GTG GGC CCG CCG ACC ATC TCG GCG ACC<br>Ala Asp Val Lys Val Pro Ser Val Gly Pro Pro Thr Ile Ser Ala Thr<br>435                      440                      445 | 1344 |
| CGT CCG CGT CCG GAT CAT CCG GAC TGG GAC GTC GCG ATC TGG CTG AAC<br>Arg Pro Arg Pro Asp His Pro Asp Trp Asp Val Ala Ile Trp Leu Asn<br>450                      455                      460 | 1392 |
| GTT CTC GGT GTT CCG GGC ACC CCC GGC ATG TTC GAG TTC TAC CGC GAG<br>Val Leu Gly Val Pro Gly Thr Pro Gly Met Phe Glu Phe Tyr Arg Glu<br>465                      470                      475                      480 | 1440 |
| ATG GAG CAG TGG ATG CGG AGC CAC TAC AAC AAC GAC GAC GCC ACC TTC<br>Met Glu Gln Trp Met Arg Ser His Tyr Asn Asn Asp Asp Ala Thr Phe<br>485                      490                      495 | 1488 |
| CGG CCC GAG TGG TCG AAG GGG TGG GCG TTC GGT CCC GAC CCG TAC ACC<br>Arg Pro Glu Trp Ser Lys Gly Trp Ala Phe Gly Pro Asp Pro Tyr Thr<br>500                      505                      510 | 1536 |
| GAC AAC GAC ATC GTC ACG AAC AAG ATG CGC GCC ACC TAC ATC GAA GGT<br>Asp Asn Asp Ile Val Thr Asn Lys Met Arg Ala Thr Tyr Ile Glu Gly<br>515                      520                      525 | 1584 |
| GTC CCG ACG ACC GAG AAC TGG GAC ACC GCG CGC GCT CGG TAC AAC CAG<br>Val Pro Thr Thr Glu Asn Trp Asp Thr Ala Arg Ala Arg Tyr Asn Gln<br>530                      535                      540 | 1632 |
| ATC GAC CCG CAT CGC GTG TTC ACC AAC GGA TTC ATG GAC AAG CTG CTT<br>Ile Asp Pro His Arg Val Phe Thr Asn Gly Phe Met Asp Lys Leu Leu | 1680 |

| 545 | 550 | 555 | 560 | |
|---|---|---|---|---|
| CCG | | | | 1683 |
| Pro | | | | |

(2) INFORMATION FOR SEQ ID NO: 2:

(i) SEQUENCE CHARACTERISTICS:
        (A) LENGTH: 561 amino acids
        (B) TYPE: amino acid
        (D) TOPOLOGY: linear (ii) MOLECULE TYPE: protein (xi) SEQUENCE DESCRIPTION: SEQ ID NO: 2:

```
Ser Thr Gly Pro Val Ala Pro Leu Pro Thr Pro Pro Asn Phe Pro Asn
 1               5                  10                  15

Asp Ile Ala Leu Phe Gln Gln Ala Tyr Gln Asn Trp Ser Lys Glu Ile
            20                  25                  30

Met Leu Asp Ala Thr Trp Val Cys Ser Pro Lys Thr Pro Gln Asp Val
        35                  40                  45

Val Arg Leu Ala Asn Trp Ala His Glu His Asp Tyr Lys Ile Arg Pro
    50                  55                  60

Arg Gly Ala Met His Gly Trp Thr Pro Leu Thr Val Glu Lys Gly Ala
65                  70                  75                  80

Asn Val Glu Lys Val Ile Leu Ala Asp Thr Met Thr His Leu Asn Gly
                85                  90                  95

Ile Thr Val Asn Thr Gly Gly Pro Val Ala Thr Val Thr Ala Gly Ala
            100                 105                 110

Gly Ala Ser Ile Glu Ala Ile Val Thr Glu Leu Gln Lys His Asp Leu
        115                 120                 125

Gly Trp Ala Asn Leu Pro Ala Pro Gly Val Leu Ser Ile Gly Gly Ala
    130                 135                 140

Leu Ala Val Asn Ala His Gly Ala Ala Leu Pro Ala Val Gly Gln Thr
145                 150                 155                 160

Thr Leu Pro Gly His Thr Tyr Gly Ser Leu Ser Asn Leu Val Thr Glu
                165                 170                 175

Leu Thr Ala Val Val Trp Asn Gly Thr Thr Tyr Ala Leu Glu Thr Tyr
            180                 185                 190

Gln Arg Asn Asp Pro Arg Ile Thr Pro Leu Leu Thr Asn Leu Gly Arg
        195                 200                 205

Cys Phe Leu Thr Ser Val Thr Met Gln Ala Gly Pro Asn Phe Arg Gln
    210                 215                 220

Arg Cys Gln Ser Tyr Thr Asp Ile Pro Trp Arg Glu Leu Phe Ala Pro
225                 230                 235                 240

Lys Gly Ala Asp Gly Arg Thr Phe Glu Lys Phe Val Ala Glu Ser Gly
                245                 250                 255

Gly Ala Glu Ala Ile Trp Tyr Pro Phe Thr Glu Lys Pro Trp Met Lys
            260                 265                 270

Val Trp Thr Val Ser Pro Thr Lys Pro Asp Ser Ser Asn Glu Val Gly
        275                 280                 285

Ser Leu Gly Ser Ala Gly Ser Leu Val Gly Lys Pro Pro Gln Ala Arg
    290                 295                 300

Glu Val Ser Gly Pro Tyr Asn Tyr Ile Phe Ser Asp Asn Leu Pro Glu
305                 310                 315                 320

Pro Ile Thr Asp Met Ile Gly Ala Ile Asn Ala Gly Asn Pro Gly Ile
                325                 330                 335
```

-continued

```
Ala Pro Leu Phe Gly Pro Ala Met Tyr Glu Ile Thr Lys Leu Gly Leu
        340                 345                 350

Ala Ala Thr Asn Ala Asn Asp Ile Trp Gly Trp Ser Lys Asp Val Gln
        355                 360                 365

Phe Tyr Ile Lys Ala Thr Thr Leu Arg Leu Thr Glu Gly Gly Gly Ala
        370                 375                 380

Val Val Thr Ser Arg Ala Asn Ile Ala Thr Val Ile Asn Asp Phe Thr
385                 390                 395                 400

Glu Trp Phe His Glu Arg Ile Glu Phe Tyr Arg Ala Lys Gly Glu Phe
                405                 410                 415

Pro Leu Asn Gly Pro Val Glu Ile Arg Cys Cys Gly Leu Asp Gln Ala
                420                 425                 430

Ala Asp Val Lys Val Pro Ser Val Gly Pro Pro Thr Ile Ser Ala Thr
                435                 440                 445

Arg Pro Arg Pro Asp His Pro Asp Trp Asp Val Ala Ile Trp Leu Asn
450                 455                 460

Val Leu Gly Val Pro Gly Thr Pro Gly Met Phe Glu Phe Tyr Arg Glu
465                 470                 475                 480

Met Glu Gln Trp Met Arg Ser His Tyr Asn Asn Asp Asp Ala Thr Phe
                485                 490                 495

Arg Pro Glu Trp Ser Lys Gly Trp Ala Phe Gly Pro Asp Pro Tyr Thr
                500                 505                 510

Asp Asn Asp Ile Val Thr Asn Lys Met Arg Ala Thr Tyr Ile Glu Gly
                515                 520                 525

Val Pro Thr Thr Glu Asn Trp Asp Thr Ala Arg Ala Arg Tyr Asn Gln
                530                 535                 540

Ile Asp Pro His Arg Val Phe Thr Asn Gly Phe Met Asp Lys Leu Leu
545                 550                 555                 560

Pro
```

(2) INFORMATION FOR SEQ ID NO: 3:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 3:

TTCCCGCTCA ACGGTCCGGT CGAGATCCGC TGCTGCGGGC TCGATCAG        48

(2) INFORMATION FOR SEQ ID NO: 4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 4:

GCGATCTGGC TGAACGTTCT CGGTGTTCCG GGCACCCCCG GCATGTTC        48

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 5:

```
GACGCCACCT TCCGGCCCGA GTGGTCGAAG GGGTGG                                      36

(2) INFORMATION FOR SEQ ID NO: 6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 17..46

(xi) SEQUENCE DESCRIPTION: SEQ ID NO: 6:

CACACAGGAA ACAGCT ATG ACC ATG ATT ACG CCA AGC TTG CAT GCC               46
              Met Thr Met Ile Thr Pro Ser Leu His Ala
                1               5                  10

(2) INFORMATION FOR SEQ ID NO: 7:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 7:

Met Thr Met Ile Thr Pro Ser Leu His Ala
  1               5                  10

(2) INFORMATION FOR SEQ ID NO: 8:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..49

(xi) SEQUENCE DESCRIPTION: SEQ ID NO: 8:

GAATTTAAGG GGAACATCG ATG ACC ATG ATT ACG CCA AGC TTG CAT GCC            49
                    Met Thr Met Ile Thr Pro Ser Leu His Ala
                      1               5                  10

(2) INFORMATION FOR SEQ ID NO: 9:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 9:

Met Thr Met Ile Thr Pro Ser Leu His Ala
  1               5                  10

(2) INFORMATION FOR SEQ ID NO: 10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear
```

(ix) FEATURE:
    (A) NAME/KEY: CDS
    (B) LOCATION: 20..43

(xi) SEQUENCE DESCRIPTION: SEQ ID NO: 10:

GAATTTAAGG GGAACATCG ATG AGT AAT CAC CAT GGG CAT GCC        43
                    Met Ser Asn His His Gly His Ala
                     1               5

(2) INFORMATION FOR SEQ ID NO: 11:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 11:

Met Ser Asn His His Gly His Ala
 1               5

(2) INFORMATION FOR SEQ ID NO: 12:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 19..45

(xi) SEQUENCE DESCRIPTION: SEQ ID NO: 12:

AATTTGGAGG GGAACATT ATG AGT AAT CAT CAC CAT GGG CAT GCC     45
                   Met Ser Asn His His His Gly His Ala
                    1               5

(2) INFORMATION FOR SEQ ID NO: 13:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 13:

Met Ser Asn His His His Gly His Ala
 1               5

(2) INFORMATION FOR SEQ ID NO: 14:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..58

(xi) SEQUENCE DESCRIPTION: SEQ ID NO: 14:

GAATTTAAGG GGAACATCG ATG AGT AAT ACG CGT AAA CGC AAG CGC CGT ACG    52
                    Met Ser Asn Thr Arg Lys Arg Lys Arg Arg Thr
                     1               5                  10
CAT GCC                                                              58
His Ala (2) INFORMATION FOR SEQ ID NO: 15:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Ser Asn Thr Arg Lys Arg Lys Arg Arg Thr His Ala
 1               5                  10
```

(2) INFORMATION FOR SEQ ID NO: 16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 25..48

(xi) SEQUENCE DESCRIPTION: SEQ ID NO: 16:

```
GAATTCACAC AGGAAACAGA ATTC ATG GTT ATG CAC CAT GGG CAT GCC        48
                           Met Val Met His His Gly His Ala
                            1               5
```

(2) INFORMATION FOR SEQ ID NO: 17:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Val Met His His Gly His Ala
 1               5
```

(2) INFORMATION FOR SEQ ID NO: 18:

(i) SEQUENCE CHARACTERISTICS:
        (A) LENGTH: 1729 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 17..1729

(xi) SEQUENCE DESCRIPTION: SEQ ID NO: 18:

```
CACACAGGAA ACAGCT ATG ACC ATG ATT ACG CCA AGC TTG CAT GCC TCG       49
               Met Thr Met Ile Thr Pro Ser Leu His Ala Ser
                1               5                  10

ACC GGG CCG GTC GCG CCG CTT CCG ACG CCG CCG AAC TTC CCG AAC GAC     97
Thr Gly Pro Val Ala Pro Leu Pro Thr Pro Pro Asn Phe Pro Asn Asp
                15                  20                  25

ATC GCG CTG TTC CAG CAG GCG TAC CAG AAC TGG TCC AAG GAG ATC ATG    145
Ile Ala Leu Phe Gln Gln Ala Tyr Gln Asn Trp Ser Lys Glu Ile Met
            30                  35                  40

CTG GAC GCC ACT TGG GTC TGC TCG CCC AAG ACG CCG CAG GAT GTC GTT    193
Leu Asp Ala Thr Trp Val Cys Ser Pro Lys Thr Pro Gln Asp Val Val
    45                  50                  55
```

-continued

```
CGC CTT GCC AAC TGG GCG CAC GAG CAC GAC TAC AAG ATC CGC CCG CGC        241
Arg Leu Ala Asn Trp Ala His Glu His Asp Tyr Lys Ile Arg Pro Arg
 60              65                  70                  75

GGC GCG ATG CAC GGC TGG ACC CCG CTC ACC GTG GAG AAG GGG GCC AAC        289
Gly Ala Met His Gly Trp Thr Pro Leu Thr Val Glu Lys Gly Ala Asn
             80                  85                  90

GTC GAG AAG GTG ATC CTC GCC GAC ACG ATG ACG CAT CTG AAC GGC ATC        337
Val Glu Lys Val Ile Leu Ala Asp Thr Met Thr His Leu Asn Gly Ile
                 95                 100                 105

ACG GTG AAC ACG GGC GGC CCC GTG GCT ACC GTC ACC GCC GGT GCC GGC        385
Thr Val Asn Thr Gly Gly Pro Val Ala Thr Val Thr Ala Gly Ala Gly
             110                 115                 120

GCC AGC ATC GAG GCG ATC GTC ACC GAA CTG CAG AAG CAC GAC CTC GGC        433
Ala Ser Ile Glu Ala Ile Val Thr Glu Leu Gln Lys His Asp Leu Gly
     125                 130                 135

TGG GCC AAC CTG CCC GCT CCG GGT GTG CTG TCG ATC GGT GGC GCC CTT        481
Trp Ala Asn Leu Pro Ala Pro Gly Val Leu Ser Ile Gly Gly Ala Leu
140                 145                 150                 155

GCG GTC AAC GCG CAC GGT GCG GCG CTG CCG GCC GTC GGC CAG ACC ACG        529
Ala Val Asn Ala His Gly Ala Ala Leu Pro Ala Val Gly Gln Thr Thr
                 160                 165                 170

CTG CCC GGT CAC ACC TAC GGT TCG CTG AGC AAC CTG GTC ACC GAG CTG        577
Leu Pro Gly His Thr Tyr Gly Ser Leu Ser Asn Leu Val Thr Glu Leu
             175                 180                 185

ACC GCG GTC GTC TGG AAC GGC ACC ACC TAC GCA CTC GAG ACG TAC CAG        625
Thr Ala Val Val Trp Asn Gly Thr Thr Tyr Ala Leu Glu Thr Tyr Gln
         190                 195                 200

CGC AAC GAT CCT CGG ATC ACC CCA CTG CTC ACC AAC CTC GGG CGC TGC        673
Arg Asn Asp Pro Arg Ile Thr Pro Leu Leu Thr Asn Leu Gly Arg Cys
     205                 210                 215

TTC CTG ACC TCG GTG ACG ATG CAG GCC GGC CCC AAC TTC CGT CAG CGG        721
Phe Leu Thr Ser Val Thr Met Gln Ala Gly Pro Asn Phe Arg Gln Arg
220                 225                 230                 235

TGC CAG AGC TAC ACC GAC ATC CCG TGG CGG GAA CTG TTC GCG CCG AAG        769
Cys Gln Ser Tyr Thr Asp Ile Pro Trp Arg Glu Leu Phe Ala Pro Lys
                 240                 245                 250

GGC GCC GAC GGC CGC ACG TTC GAG AAG TTC GTC GCG GAA TCG GGC GGC        817
Gly Ala Asp Gly Arg Thr Phe Glu Lys Phe Val Ala Glu Ser Gly Gly
             255                 260                 265

GCC GAG GCG ATC TGG TAC CCG TTC ACC GAG AAG CCG TGG ATG AAG GTG        865
Ala Glu Ala Ile Trp Tyr Pro Phe Thr Glu Lys Pro Trp Met Lys Val
         270                 275                 280

TGG ACG GTC TCG CCG ACC AAG CCG GAC TCG TCG AAC GAG GTC GGA AGC        913
Trp Thr Val Ser Pro Thr Lys Pro Asp Ser Ser Asn Glu Val Gly Ser
     285                 290                 295

CTC GGC TCG GCG GGC TCC CTC GTC GGC AAG CCT CCG CAG GCG CGT GAG        961
Leu Gly Ser Ala Gly Ser Leu Val Gly Lys Pro Pro Gln Ala Arg Glu
300                 305                 310                 315

GTC TCC GGC CCG TAC AAC TAC ATC TTC TCC GAC AAC CTG CCG GAG CCC       1009
Val Ser Gly Pro Tyr Asn Tyr Ile Phe Ser Asp Asn Leu Pro Glu Pro
                 320                 325                 330

ATC ACC GAC ATG ATC GGC GCC ATC AAC GCC GGA AAC CCC GGA ATC GCA       1057
Ile Thr Asp Met Ile Gly Ala Ile Asn Ala Gly Asn Pro Gly Ile Ala
             335                 340                 345

CCG CTG TTC GGC CCG GCG ATG TAC GAG ATC ACC AAG CTC GGG CTG GCC       1105
Pro Leu Phe Gly Pro Ala Met Tyr Glu Ile Thr Lys Leu Gly Leu Ala
         350                 355                 360

GCG ACG AAT GCC AAC GAC ATC TGG GGC TGG TCG AAG GAC GTC CAG TTC       1153
Ala Thr Asn Ala Asn Asp Ile Trp Gly Trp Ser Lys Asp Val Gln Phe
     365                 370                 375
```

-continued

```
TAC ATC AAG GCC ACG ACG TTG CGA CTC ACC GAG GGC GGC GGC GCC GTC      1201
Tyr Ile Lys Ala Thr Thr Leu Arg Leu Thr Glu Gly Gly Gly Ala Val
380                 385                 390                 395

GTC ACG AGC CGC GCC AAC ATC GCG ACC GTG ATC AAC GAC TTC ACC GAG      1249
Val Thr Ser Arg Ala Asn Ile Ala Thr Val Ile Asn Asp Phe Thr Glu
                400                 405                 410

TGG TTC CAC GAG CGC ATC GAG TTC TAC CGC GCG AAG GGC GAG TTC CCG      1297
Trp Phe His Glu Arg Ile Glu Phe Tyr Arg Ala Lys Gly Glu Phe Pro
            415                 420                 425

CTC AAC GGT CCG GTC GAG ATC CGC TGC TGC GGG CTC GAT CAG GCA GCC      1345
Leu Asn Gly Pro Val Glu Ile Arg Cys Cys Gly Leu Asp Gln Ala Ala
        430                 435                 440

GAC GTC AAG GTG CCG TCG GTG GGC CCG CCG ACC ATC TCG GCG ACC CGT      1393
Asp Val Lys Val Pro Ser Val Gly Pro Pro Thr Ile Ser Ala Thr Arg
    445                 450                 455

CCG CGT CCG GAT CAT CCG GAC TGG GAC GTC GCG ATC TGG CTG AAC GTT      1441
Pro Arg Pro Asp His Pro Asp Trp Asp Val Ala Ile Trp Leu Asn Val
460                 465                 470                 475

CTC GGT GTT CCG GGC ACC CCC GGC ATG TTC GAG TTC TAC CGC GAG ATG      1489
Leu Gly Val Pro Gly Thr Pro Gly Met Phe Glu Phe Tyr Arg Glu Met
                480                 485                 490

GAG CAG TGG ATG CGG AGC CAC TAC AAC AAC GAC GAC GCC ACC TTC CGG      1537
Glu Gln Trp Met Arg Ser His Tyr Asn Asn Asp Asp Ala Thr Phe Arg
            495                 500                 505

CCC GAG TGG TCG AAG GGG TGG GCG TTC GGT CCC GAC CCG TAC ACC GAC      1585
Pro Glu Trp Ser Lys Gly Trp Ala Phe Gly Pro Asp Pro Tyr Thr Asp
        510                 515                 520

AAC GAC ATC GTC ACG AAC AAG ATG CGC GCC ACC TAC ATC GAA GGT GTC      1633
Asn Asp Ile Val Thr Asn Lys Met Arg Ala Thr Tyr Ile Glu Gly Val
    525                 530                 535

CCG ACG ACC GAG AAC TGG GAC ACC GCG CGC GCT CGG TAC AAC CAG ATC      1681
Pro Thr Thr Glu Asn Trp Asp Thr Ala Arg Ala Arg Tyr Asn Gln Ile
540                 545                 550                 555

GAC CCG CAT CGC GTG TTC ACC AAC GGA TTC ATG GAC AAG CTG CTT CCG      1729
Asp Pro His Arg Val Phe Thr Asn Gly Phe Met Asp Lys Leu Leu Pro
                560                 565                 570
```

(2) INFORMATION FOR SEQ ID NO: 19:

(i) SEQUENCE CHARACTERISTICS:
        (A) LENGTH: 571 amino acids
        (B) TYPE: amino acid
        (D) TOPOLOGY: linear (ii) MOLECULE TYPE: Protein (xi) SEQUENCE DESCRIPTION: SEQ ID NO: 19:

```
Met Thr Met Ile Thr Pro Ser Leu His Ala Ser Thr Gly Pro Val Ala
1               5                   10                  15

Pro Leu Pro Thr Pro Pro Asn Phe Pro Asn Asp Ile Ala Leu Phe Gln
            20                  25                  30

Gln Ala Tyr Gln Asn Trp Ser Lys Glu Ile Met Leu Asp Ala Thr Trp
        35                  40                  45

Val Cys Ser Pro Lys Thr Pro Gln Asp Val Val Arg Leu Ala Asn Trp
    50                  55                  60

Ala His Glu His Asp Tyr Lys Ile Arg Pro Arg Gly Ala Met His Gly
65                  70                  75                  80

Trp Thr Pro Leu Thr Val Glu Lys Gly Ala Asn Val Glu Lys Val Ile
                85                  90                  95

Leu Ala Asp Thr Met Thr His Leu Asn Gly Ile Thr Val Asn Thr Gly
```

```
                    100             105             110
Gly Pro Val Ala Thr Val Thr Ala Gly Ala Gly Ala Ser Ile Glu Ala
            115             120             125
Ile Val Thr Glu Leu Gln Lys His Asp Leu Gly Trp Ala Asn Leu Pro
130             135             140
Ala Pro Gly Val Leu Ser Ile Gly Gly Ala Leu Ala Val Asn Ala His
145             150             155             160
Gly Ala Ala Leu Pro Ala Val Gly Gln Thr Thr Leu Pro Gly His Thr
            165             170             175
Tyr Gly Ser Leu Ser Asn Leu Val Thr Glu Leu Thr Ala Val Val Trp
            180             185             190
Asn Gly Thr Thr Tyr Ala Leu Glu Thr Tyr Gln Arg Asn Asp Pro Arg
            195             200             205
Ile Thr Pro Leu Leu Thr Asn Leu Gly Arg Cys Phe Leu Thr Ser Val
            210             215             220
Thr Met Gln Ala Gly Pro Asn Phe Arg Gln Arg Cys Gln Ser Tyr Thr
225             230             235             240
Asp Ile Pro Trp Arg Glu Leu Phe Ala Pro Lys Gly Ala Asp Gly Arg
            245             250             255
Thr Phe Glu Lys Phe Val Ala Glu Ser Gly Gly Ala Glu Ala Ile Trp
            260             265             270
Tyr Pro Phe Thr Glu Lys Pro Trp Met Lys Val Trp Thr Val Ser Pro
            275             280             285
Thr Lys Pro Asp Ser Ser Asn Glu Val Gly Ser Leu Gly Ser Ala Gly
            290             295             300
Ser Leu Val Gly Lys Pro Pro Gln Ala Arg Glu Val Ser Gly Pro Tyr
305             310             315             320
Asn Tyr Ile Phe Ser Asp Asn Leu Pro Glu Pro Ile Thr Asp Met Ile
            325             330             335
Gly Ala Ile Asn Ala Gly Asn Pro Gly Ile Ala Pro Leu Phe Gly Pro
            340             345             350
Ala Met Tyr Glu Ile Thr Lys Leu Gly Leu Ala Ala Thr Asn Ala Asn
            355             360             365
Asp Ile Trp Gly Trp Ser Lys Asp Val Gln Phe Tyr Ile Lys Ala Thr
370             375             380
Thr Leu Arg Leu Thr Glu Gly Gly Ala Val Val Thr Ser Arg Ala
385             390             395             400
Asn Ile Ala Thr Val Ile Asn Asp Phe Thr Glu Trp Phe His Glu Arg
            405             410             415
Ile Glu Phe Tyr Arg Ala Lys Gly Glu Phe Pro Leu Asn Gly Pro Val
            420             425             430
Glu Ile Arg Cys Cys Gly Leu Asp Gln Ala Ala Asp Val Lys Val Pro
            435             440             445
Ser Val Gly Pro Pro Thr Ile Ser Ala Thr Arg Pro Arg Pro Asp His
450             455             460
Pro Asp Trp Asp Val Ala Ile Trp Leu Asn Val Leu Gly Val Pro Gly
465             470             475             480
Thr Pro Gly Met Phe Glu Phe Tyr Arg Glu Met Glu Gln Trp Met Arg
            485             490             495
Ser His Tyr Asn Asn Asp Asp Ala Thr Phe Arg Pro Glu Trp Ser Lys
            500             505             510
Gly Trp Ala Phe Gly Pro Asp Pro Tyr Thr Asp Asn Asp Ile Val Thr
            515             520             525
```

```
Asn Lys Met Arg Ala Thr Tyr Ile Glu Gly Val Pro Thr Thr Glu Asn
530                 535                 540

Trp Asp Thr Ala Arg Ala Arg Tyr Asn Gln Ile Asp Pro His Arg Val
545                 550                 555                 560

Phe Thr Asn Gly Phe Met Asp Lys Leu Leu Pro
                565                 570
```

(2) INFORMATION FOR SEQ ID NO: 20:

(i) SEQUENCE CHARACTERISTICS:
        (A) LENGTH: 1732 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..1732

(xi) SEQUENCE DESCRIPTION: SEQ ID NO: 20:

```
GAATTTAAGG GGAACATCG ATG ACC ATG ATT ACG CCA AGC TTG CAT GCC TCG        52
                    Met Thr Met Ile Thr Pro Ser Leu His Ala Ser
                    1               5                   10

ACC GGG CCG GTC GCG CCG CTT CCG ACG CCG CCG AAC TTC CCG AAC GAC        100
Thr Gly Pro Val Ala Pro Leu Pro Thr Pro Pro Asn Phe Pro Asn Asp
                15                  20                  25

ATC GCG CTG TTC CAG CAG GCG TAC CAG AAC TGG TCC AAG GAG ATC ATG        148
Ile Ala Leu Phe Gln Gln Ala Tyr Gln Asn Trp Ser Lys Glu Ile Met
            30                  35                  40

CTG GAC GCC ACT TGG GTC TGC TCG CCC AAG ACG CCG CAG GAT GTC GTT        196
Leu Asp Ala Thr Trp Val Cys Ser Pro Lys Thr Pro Gln Asp Val Val
        45                  50                  55

CGC CTT GCC AAC TGG GCG CAC GAG CAC GAC TAC AAG ATC CGC CCG CGC        244
Arg Leu Ala Asn Trp Ala His Glu His Asp Tyr Lys Ile Arg Pro Arg
    60                  65                  70                  75

GGC GCG ATG CAC GGC TGG ACC CCG CTC ACC GTG GAG AAG GGG GCC AAC        292
Gly Ala Met His Gly Trp Thr Pro Leu Thr Val Glu Lys Gly Ala Asn
                80                  85                  90

GTC GAG AAG GTG ATC CTC GCC GAC ACG ATG ACG CAT CTG AAC GGC ATC        340
Val Glu Lys Val Ile Leu Ala Asp Thr Met Thr His Leu Asn Gly Ile
            95                  100                 105

ACG GTG AAC ACG GGC GGC CCC GTG GCT ACC GTC ACC GCC GGT GCC GGC        388
Thr Val Asn Thr Gly Gly Pro Val Ala Thr Val Thr Ala Gly Ala Gly
        110                 115                 120

GCC AGC ATC GAG GCG ATC GTC ACC GAA CTG CAG AAG CAC GAC CTC GGC        436
Ala Ser Ile Glu Ala Ile Val Thr Glu Leu Gln Lys His Asp Leu Gly
    125                 130                 135

TGG GCC AAC CTG CCC GCT CCG GGT GTG CTG TCG ATC GGT GGC GCC CTT        484
Trp Ala Asn Leu Pro Ala Pro Gly Val Leu Ser Ile Gly Gly Ala Leu
140                 145                 150                 155

GCG GTC AAC GCG CAC GGT GCG GCG CTG CCG GCC GTC GGC CAG ACC ACG        532
Ala Val Asn Ala His Gly Ala Ala Leu Pro Ala Val Gly Gln Thr Thr
                160                 165                 170

CTG CCC GGT CAC ACC TAC GGT TCG CTG AGC AAC CTG GTC ACC GAG CTG        580
Leu Pro Gly His Thr Tyr Gly Ser Leu Ser Asn Leu Val Thr Glu Leu
            175                 180                 185

ACC GCG GTC GTC TGG AAC GGC ACC ACC TAC GCA CTC GAG ACG TAC CAG        628
Thr Ala Val Val Trp Asn Gly Thr Thr Tyr Ala Leu Glu Thr Tyr Gln
        190                 195                 200

CGC AAC GAT CCT CGG ATC ACC CCA CTG CTC ACC AAC CTC GGG CGC TGC        676
Arg Asn Asp Pro Arg Ile Thr Pro Leu Leu Thr Asn Leu Gly Arg Cys
    205                 210                 215
```

-continued

| | |
|---|---|
| TTC CTG ACC TCG GTG ACG ATG CAG GCC GGC CCC AAC TTC CGT CAG CGG<br>Phe Leu Thr Ser Val Thr Met Gln Ala Gly Pro Asn Phe Arg Gln Arg<br>220                        225                        230                        235 | 724 |
| TGC CAG AGC TAC ACC GAC ATC CCG TGG CGG GAA CTG TTC GCG CCG AAG<br>Cys Gln Ser Tyr Thr Asp Ile Pro Trp Arg Glu Leu Phe Ala Pro Lys<br>                 240                        245                        250 | 772 |
| GGC GCC GAC GGC CGC ACG TTC GAG AAG TTC GTC GCG GAA TCG GGC GGC<br>Gly Ala Asp Gly Arg Thr Phe Glu Lys Phe Val Ala Glu Ser Gly Gly<br>                       255                       260                     265 | 820 |
| GCC GAG GCG ATC TGG TAC CCG TTC ACC GAG AAG CCG TGG ATG AAG GTG<br>Ala Glu Ala Ile Trp Tyr Pro Phe Thr Glu Lys Pro Trp Met Lys Val<br>                 270                     275                   280 | 868 |
| TGG ACG GTC TCG CCG ACC AAG CCG GAC TCG TCG AAC GAG GTC GGA AGC<br>Trp Thr Val Ser Pro Thr Lys Pro Asp Ser Ser Asn Glu Val Gly Ser<br>285                        290                     295 | 916 |
| CTC GGC TCG GCG GGC TCC CTC GTC GGC AAG CCT CCG CAG GCG CGT GAG<br>Leu Gly Ser Ala Gly Ser Leu Val Gly Lys Pro Pro Gln Ala Arg Glu<br>300                        305                     310                   315 | 964 |
| GTC TCC GGC CCG TAC AAC TAC ATC TTC TCC GAC AAC CTG CCG GAG CCC<br>Val Ser Gly Pro Tyr Asn Tyr Ile Phe Ser Asp Asn Leu Pro Glu Pro<br>                 320                     325                     330 | 1012 |
| ATC ACC GAC ATG ATC GGC GCC ATC AAC GCC GGA AAC CCC GGA ATC GCA<br>Ile Thr Asp Met Ile Gly Ala Ile Asn Ala Gly Asn Pro Gly Ile Ala<br>               335                     340                   345 | 1060 |
| CCG CTG TTC GGC CCG GCG ATG TAC GAG ATC ACC AAG CTC GGG CTG GCC<br>Pro Leu Phe Gly Pro Ala Met Tyr Glu Ile Thr Lys Leu Gly Leu Ala<br>             350                     355                   360 | 1108 |
| GCG ACG AAT GCC AAC GAC ATC TGG GGC TGG TCG AAG GAC GTC CAG TTC<br>Ala Thr Asn Ala Asn Asp Ile Trp Gly Trp Ser Lys Asp Val Gln Phe<br>365                        370                     375 | 1156 |
| TAC ATC AAG GCC ACG ACG TTG CGA CTC ACC GAG GGC GGC GGC GCC GTC<br>Tyr Ile Lys Ala Thr Thr Leu Arg Leu Thr Glu Gly Gly Gly Ala Val<br>380                        385                     390                   395 | 1204 |
| GTC ACG AGC CGC GCC AAC ATC GCG ACC GTG ATC AAC GAC TTC ACC GAG<br>Val Thr Ser Arg Ala Asn Ile Ala Thr Val Ile Asn Asp Phe Thr Glu<br>                 400                     405                     410 | 1252 |
| TGG TTC CAC GAG CGC ATC GAG TTC TAC CGC GCG AAG GGC GAG TTC CCG<br>Trp Phe His Glu Arg Ile Glu Phe Tyr Arg Ala Lys Gly Glu Phe Pro<br>             415                     420                   425 | 1300 |
| CTC AAC GGT CCG GTC GAG ATC CGC TGC TGC GGG CTC GAT CAG GCA GCC<br>Leu Asn Gly Pro Val Glu Ile Arg Cys Cys Gly Leu Asp Gln Ala Ala<br>             430                     435                   440 | 1348 |
| GAC GTC AAG GTG CCG TCG GTG GGC CCG CCG ACC ATC TCG GCG ACC CGT<br>Asp Val Lys Val Pro Ser Val Gly Pro Pro Thr Ile Ser Ala Thr Arg<br>445                       450                     455 | 1396 |
| CCG CGT CCG GAT CAT CCG GAC TGG GAC GTC GCG ATC TGG CTG AAC GTT<br>Pro Arg Pro Asp His Pro Asp Trp Asp Val Ala Ile Trp Leu Asn Val<br>460                       465                     470                   475 | 1444 |
| CTC GGT GTT CCG GGC ACC CCC GGC ATG TTC GAG TTC TAC CGC GAG ATG<br>Leu Gly Val Pro Gly Thr Pro Gly Met Phe Glu Phe Tyr Arg Glu Met<br>             480                     485                   490 | 1492 |
| GAG CAG TGG ATG CGG AGC CAC TAC AAC AAC GAC GAC GCC ACC TTC CGG<br>Glu Gln Trp Met Arg Ser His Tyr Asn Asn Asp Asp Ala Thr Phe Arg<br>             495                     500                   505 | 1540 |
| CCC GAG TGG TCG AAG GGG TGG GCG TTC GGT CCC GAC CCG TAC ACC GAC<br>Pro Glu Trp Ser Lys Gly Trp Ala Phe Gly Pro Asp Pro Tyr Thr Asp<br>             510                     515                   520 | 1588 |
| AAC GAC ATC GTC ACG AAC AAG ATG CGC GCC ACC TAC ATC GAA GGT GTC<br>Asn Asp Ile Val Thr Asn Lys Met Arg Ala Thr Tyr Ile Glu Gly Val<br>525                        530                     535 | 1636 |

```
CCG ACG ACC GAG AAC TGG GAC ACC GCG CGC GCT CGG TAC AAC CAG ATC        1684
Pro Thr Thr Glu Asn Trp Asp Thr Ala Arg Ala Arg Tyr Asn Gln Ile
540                 545                 550                 555

GAC CCG CAT CGC GTG TTC ACC AAC GGA TTC ATG GAC AAG CTG CTT CCG        1732
Asp Pro His Arg Val Phe Thr Asn Gly Phe Met Asp Lys Leu Leu Pro
                560                 565                 570
```

(2) INFORMATION FOR SEQ ID NO: 21:

(i) SEQUENCE CHARACTERISTICS:
        (A) LENGTH: 571 amino acids
        (B) TYPE: amino acids
        (D) TOPOLOGY: linear (ii) MOLECULE TYPE: Protein (xi) SEQUENCE DESCRIPTION: SEQ ID NO: 21:

```
Met Thr Met Ile Thr Pro Ser Leu His Ala Ser Thr Gly Pro Val Ala
 1               5                  10                  15

Pro Leu Pro Thr Pro Pro Asn Phe Pro Asn Asp Ile Ala Leu Phe Gln
                20                  25                  30

Gln Ala Tyr Gln Asn Trp Ser Lys Glu Ile Met Leu Asp Ala Thr Trp
             35                  40                  45

Val Cys Ser Pro Lys Thr Pro Gln Asp Val Val Arg Leu Ala Asn Trp
 50                  55                  60

Ala His Glu His Asp Tyr Lys Ile Arg Pro Arg Gly Ala Met His Gly
 65                  70                  75                  80

Trp Thr Pro Leu Thr Val Glu Lys Gly Ala Asn Val Glu Lys Val Ile
                 85                  90                  95

Leu Ala Asp Thr Met Thr His Leu Asn Gly Ile Thr Val Asn Thr Gly
                100                 105                 110

Gly Pro Val Ala Thr Val Thr Ala Gly Ala Gly Ala Ser Ile Glu Ala
                115                 120                 125

Ile Val Thr Glu Leu Gln Lys His Asp Leu Gly Trp Ala Asn Leu Pro
130                 135                 140

Ala Pro Gly Val Leu Ser Ile Gly Gly Ala Leu Ala Val Asn Ala His
145                 150                 155                 160

Gly Ala Ala Leu Pro Ala Val Gly Gln Thr Thr Leu Pro Gly His Thr
                165                 170                 175

Tyr Gly Ser Leu Ser Asn Leu Val Thr Glu Leu Thr Ala Val Val Trp
                180                 185                 190

Asn Gly Thr Thr Tyr Ala Leu Glu Thr Tyr Gln Arg Asn Asp Pro Arg
                195                 200                 205

Ile Thr Pro Leu Leu Thr Asn Leu Gly Arg Cys Phe Leu Thr Ser Val
210                 215                 220

Thr Met Gln Ala Gly Pro Asn Phe Arg Gln Arg Cys Gln Ser Tyr Thr
225                 230                 235                 240

Asp Ile Pro Trp Arg Glu Leu Phe Ala Pro Lys Gly Ala Asp Gly Arg
                245                 250                 255

Thr Phe Glu Lys Phe Val Ala Glu Ser Gly Gly Ala Glu Ala Ile Trp
                260                 265                 270

Tyr Pro Phe Thr Glu Lys Pro Trp Met Lys Val Trp Thr Val Ser Pro
                275                 280                 285

Thr Lys Pro Asp Ser Ser Asn Glu Val Gly Ser Leu Gly Ser Ala Gly
                290                 295                 300

Ser Leu Val Gly Lys Pro Pro Gln Ala Arg Glu Val Ser Gly Pro Tyr
305                 310                 315                 320
```

```
Asn Tyr Ile Phe Ser Asp Asn Leu Pro Glu Pro Ile Thr Asp Met Ile
            325                 330                 335

Gly Ala Ile Asn Ala Gly Asn Pro Gly Ile Ala Pro Leu Phe Gly Pro
            340                 345                 350

Ala Met Tyr Glu Ile Thr Lys Leu Gly Leu Ala Ala Thr Asn Ala Asn
            355                 360                 365

Asp Ile Trp Gly Trp Ser Lys Asp Val Gln Phe Tyr Ile Lys Ala Thr
            370                 375                 380

Thr Leu Arg Leu Thr Glu Gly Gly Ala Val Val Thr Ser Arg Ala
385                 390                 395                 400

Asn Ile Ala Thr Val Ile Asn Asp Phe Thr Glu Trp Phe His Glu Arg
            405                 410                 415

Ile Glu Phe Tyr Arg Ala Lys Gly Glu Phe Pro Leu Asn Gly Pro Val
            420                 425                 430

Glu Ile Arg Cys Cys Gly Leu Asp Gln Ala Ala Asp Val Lys Val Pro
            435                 440                 445

Ser Val Gly Pro Pro Thr Ile Ser Ala Thr Arg Pro Arg Pro Asp His
            450                 455                 460

Pro Asp Trp Asp Val Ala Ile Trp Leu Asn Val Leu Gly Val Pro Gly
465                 470                 475                 480

Thr Pro Gly Met Phe Glu Phe Tyr Arg Glu Met Glu Gln Trp Met Arg
            485                 490                 495

Ser His Tyr Asn Asn Asp Asp Ala Thr Phe Arg Pro Glu Trp Ser Lys
            500                 505                 510

Gly Trp Ala Phe Gly Pro Asp Pro Tyr Thr Asp Asn Asp Ile Val Thr
            515                 520                 525

Asn Lys Met Arg Ala Thr Tyr Ile Glu Gly Val Pro Thr Thr Glu Asn
            530                 535                 540

Trp Asp Thr Ala Arg Ala Arg Tyr Asn Gln Ile Asp Pro His Arg Val
545                 550                 555                 560

Phe Thr Asn Gly Phe Met Asp Lys Leu Leu Pro
            565                 570

(2) INFORMATION FOR SEQ ID NO: 22:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..1726

(xi) SEQUENCE DESCRIPTION: SEQ ID NO: 22:

GAATTTAAGG GGAACATCG ATG AGT AAT CAC CAT GGG CAT GCC TCG ACC GGG      52
                    Met Ser Asn His His Gly His Ala Ser Thr Gly
                    1               5                   10

CCG GTC GCG CCG CTT CCG ACG CCG CCG AAC TTC CCG AAC GAC ATC GCG      100
Pro Val Ala Pro Leu Pro Thr Pro Pro Asn Phe Pro Asn Asp Ile Ala
            15                  20                  25

CTG TTC CAG CAG GCG TAC CAG AAC TGG TCC AAG GAG ATC ATG CTG GAC      148
Leu Phe Gln Gln Ala Tyr Gln Asn Trp Ser Lys Glu Ile Met Leu Asp
        30                  35                  40

GCC ACT TGG GTC TGC TCG CCC AAG ACG CCG CAG GAT GTC GTT CGC CTT      196
Ala Thr Trp Val Cys Ser Pro Lys Thr Pro Gln Asp Val Val Arg Leu
    45                  50                  55

GCC AAC TGG GCG CAC GAG CAC GAC TAC AAG ATC CGC CCG CGC GGC GCG      244
```

```
Ala Asn Trp Ala His Glu His Asp Tyr Lys Ile Arg Pro Arg Gly Ala
 60              65                  70                  75

ATG CAC GGC TGG ACC CCG CTC ACC GTG GAG AAG GGG GCC AAC GTC GAG    292
Met His Gly Trp Thr Pro Leu Thr Val Glu Lys Gly Ala Asn Val Glu
                 80                  85                  90

AAG GTG ATC CTC GCC GAC ACG ATG ACG CAT CTG AAC GGC ATC ACG GTG    340
Lys Val Ile Leu Ala Asp Thr Met Thr His Leu Asn Gly Ile Thr Val
                     95                 100                 105

AAC ACG GGC GGC CCC GTG GCT ACC GTC ACC GCC GGT GCC GGC GCC AGC    388
Asn Thr Gly Gly Pro Val Ala Thr Val Thr Ala Gly Ala Gly Ala Ser
            110                 115                 120

ATC GAG GCG ATC GTC ACC GAA CTG CAG AAG CAC GAC CTC GGC TGG GCC    436
Ile Glu Ala Ile Val Thr Glu Leu Gln Lys His Asp Leu Gly Trp Ala
        125                 130                 135

AAC CTG CCC GCT CCG GGT GTG CTG TCG ATC GGT GGC GCC CTT GCG GTC    484
Asn Leu Pro Ala Pro Gly Val Leu Ser Ile Gly Gly Ala Leu Ala Val
140                 145                 150                 155

AAC GCG CAC GGT GCG GCG CTG CCG GCC GTC GGC CAG ACC ACG CTG CCC    532
Asn Ala His Gly Ala Ala Leu Pro Ala Val Gly Gln Thr Thr Leu Pro
                160                 165                 170

GGT CAC ACC TAC GGT TCG CTG AGC AAC CTG GTC ACC GAG CTG ACC GCG    580
Gly His Thr Tyr Gly Ser Leu Ser Asn Leu Val Thr Glu Leu Thr Ala
                    175                 180                 185

GTC GTC TGG AAC GGC ACC ACC TAC GCA CTC GAG ACG TAC CAG CGC AAC    628
Val Val Trp Asn Gly Thr Thr Tyr Ala Leu Glu Thr Tyr Gln Arg Asn
                190                 195                 200

GAT CCT CGG ATC ACC CCA CTG CTC ACC AAC CTC GGG CGC TGC TTC CTG    676
Asp Pro Arg Ile Thr Pro Leu Leu Thr Asn Leu Gly Arg Cys Phe Leu
        205                 210                 215

ACC TCG GTG ACG ATG CAG GCC GGC CCC AAC TTC CGT CAG CGG TGC CAG    724
Thr Ser Val Thr Met Gln Ala Gly Pro Asn Phe Arg Gln Arg Cys Gln
220                 225                 230                 235

AGC TAC ACC GAC ATC CCG TGG CGG GAA CTG TTC GCG CCG AAG GGC GCC    772
Ser Tyr Thr Asp Ile Pro Trp Arg Glu Leu Phe Ala Pro Lys Gly Ala
                240                 245                 250

GAC GGC CGC ACG TTC GAG AAG TTC GTC GCG GAA TCG GGC GGC GCC GAG    820
Asp Gly Arg Thr Phe Glu Lys Phe Val Ala Glu Ser Gly Gly Ala Glu
                    255                 260                 265

GCG ATC TGG TAC CCG TTC ACC GAG AAG CCG TGG ATG AAG GTG TGG ACG    868
Ala Ile Trp Tyr Pro Phe Thr Glu Lys Pro Trp Met Lys Val Trp Thr
                270                 275                 280

GTC TCG CCG ACC AAG CCG GAC TCG TCG AAC GAG GTC GGA AGC CTC GGC    916
Val Ser Pro Thr Lys Pro Asp Ser Ser Asn Glu Val Gly Ser Leu Gly
        285                 290                 295

TCG GCG GGC TCC CTC GTC GGC AAG CCT CCG CAG GCG CGT GAG GTC TCC    964
Ser Ala Gly Ser Leu Val Gly Lys Pro Pro Gln Ala Arg Glu Val Ser
300                 305                 310                 315

GGC CCG TAC AAC TAC ATC TTC TCC GAC AAC CTG CCG GAG CCC ATC ACC   1012
Gly Pro Tyr Asn Tyr Ile Phe Ser Asp Asn Leu Pro Glu Pro Ile Thr
                320                 325                 330

GAC ATG ATC GGC GCC ATC AAC GCC GGA AAC CCC GGA ATC GCA CCG CTG   1060
Asp Met Ile Gly Ala Ile Asn Ala Gly Asn Pro Gly Ile Ala Pro Leu
                    335                 340                 345

TTC GGC CCG GCG ATG TAC GAG ATC ACC AAG CTC GGG CTG GCC GCG ACG   1108
Phe Gly Pro Ala Met Tyr Glu Ile Thr Lys Leu Gly Leu Ala Ala Thr
                350                 355                 360

AAT GCC AAC GAC ATC TGG GGC TGG TCG AAG GAC GTC CAG TTC TAC ATC   1156
Asn Ala Asn Asp Ile Trp Gly Trp Ser Lys Asp Val Gln Phe Tyr Ile
365                 370                 375

AAG GCC ACG ACG TTG CGA CTC ACC GAG GGC GGC GGC GCC GTC GTC ACG   1204
```

```
         Lys Ala Thr Thr Leu Arg Leu Thr Glu Gly Gly Gly Ala Val Val Thr
         380                 385                 390                 395

AGC CGC GCC AAC ATC GCG ACC GTG ATC AAC GAC TTC ACC GAG TGG TTC          1252
Ser Arg Ala Asn Ile Ala Thr Val Ile Asn Asp Phe Thr Glu Trp Phe
                    400                 405                 410

CAC GAG CGC ATC GAG TTC TAC CGC GCG AAG GGC GAG TTC CCG CTC AAC          1300
His Glu Arg Ile Glu Phe Tyr Arg Ala Lys Gly Glu Phe Pro Leu Asn
                415                 420                 425

GGT CCG GTC GAG ATC CGC TGC TGC GGG CTC GAT CAG GCA GCC GAC GTC          1348
Gly Pro Val Glu Ile Arg Cys Cys Gly Leu Asp Gln Ala Ala Asp Val
            430                 435                 440

AAG GTG CCG TCG GTG GGC CCG CCG ACC ATC TCG GCG ACC CGT CCG CGT          1396
Lys Val Pro Ser Val Gly Pro Pro Thr Ile Ser Ala Thr Arg Pro Arg
        445                 450                 455

CCG GAT CAT CCG GAC TGG GAC GTC GCG ATC TGG CTG AAC GTT CTC GGT          1444
Pro Asp His Pro Asp Trp Asp Val Ala Ile Trp Leu Asn Val Leu Gly
460                 465                 470                 475

GTT CCG GGC ACC CCC GGC ATG TTC GAG TTC TAC CGC GAG ATG GAG CAG          1492
Val Pro Gly Thr Pro Gly Met Phe Glu Phe Tyr Arg Glu Met Glu Gln
                    480                 485                 490

TGG ATG CGG AGC CAC TAC AAC AAC GAC GAC GCC ACC TTC CGG CCC GAG          1540
Trp Met Arg Ser His Tyr Asn Asn Asp Asp Ala Thr Phe Arg Pro Glu
                495                 500                 505

TGG TCG AAG GGG TGG GCG TTC GGT CCC GAC CCG TAC ACC GAC AAC GAC          1588
Trp Ser Lys Gly Trp Ala Phe Gly Pro Asp Pro Tyr Thr Asp Asn Asp
            510                 515                 520

ATC GTC ACG AAC AAG ATG CGC GCC ACC TAC ATC GAA GGT GTC CCG ACG          1636
Ile Val Thr Asn Lys Met Arg Ala Thr Tyr Ile Glu Gly Val Pro Thr
        525                 530                 535

ACC GAG AAC TGG GAC ACC GCG CGC GCT CGG TAC AAC CAG ATC GAC CCG          1684
Thr Glu Asn Trp Asp Thr Ala Arg Ala Arg Tyr Asn Gln Ile Asp Pro
540                 545                 550                 555

CAT CGC GTG TTC ACC AAC GGA TTC ATG GAC AAG CTG CTT CCG                  1726
His Arg Val Phe Thr Asn Gly Phe Met Asp Lys Leu Leu Pro
                    560                 565

(2) INFORMATION FOR SEQ ID NO: 23:

(i) SEQUENCE CHARACTERISTICS:
        (A) LENGTH: 569 amino acids
        (B) TYPE: amino acid
        (D) TOPOLOGY: linear (ii) MOLECULE TYPE: Protein (xi) SEQUENCE DESCRIPTION: SEQ ID NO: 23:

Met Ser Asn His His Gly His Ala Ser Thr Gly Pro Val Ala Pro Leu
 1               5                  10                  15

Pro Thr Pro Pro Asn Phe Pro Asn Asp Ile Ala Leu Phe Gln Gln Ala
                20                  25                  30

Tyr Gln Asn Trp Ser Lys Glu Ile Met Leu Asp Ala Thr Trp Val Cys
            35                  40                  45

Ser Pro Lys Thr Pro Gln Asp Val Val Arg Leu Ala Asn Trp Ala His
        50                  55                  60

Glu His Asp Tyr Lys Ile Arg Pro Arg Gly Ala Met His Gly Trp Thr
65                  70                  75                  80

Pro Leu Thr Val Glu Lys Gly Ala Asn Val Glu Lys Val Ile Leu Ala
                85                  90                  95

Asp Thr Met Thr His Leu Asn Gly Ile Thr Val Asn Thr Gly Gly Pro
            100                 105                 110
```

-continued

```
Val Ala Thr Val Thr Ala Gly Ala Gly Ala Ser Ile Glu Ala Ile Val
            115                 120                 125

Thr Glu Leu Gln Lys His Asp Leu Gly Trp Ala Asn Leu Pro Ala Pro
130                 135                 140

Gly Val Leu Ser Ile Gly Gly Ala Leu Ala Val Asn Ala His Gly Ala
145                 150                 155                 160

Ala Leu Pro Ala Val Gly Gln Thr Thr Leu Pro Gly His Thr Tyr Gly
                165                 170                 175

Ser Leu Ser Asn Leu Val Thr Glu Leu Thr Ala Val Val Trp Asn Gly
            180                 185                 190

Thr Thr Tyr Ala Leu Glu Thr Tyr Gln Arg Asn Asp Pro Arg Ile Thr
        195                 200                 205

Pro Leu Leu Thr Asn Leu Gly Arg Cys Phe Leu Thr Ser Val Thr Met
210                 215                 220

Gln Ala Gly Pro Asn Phe Arg Gln Arg Cys Gln Ser Tyr Thr Asp Ile
225                 230                 235                 240

Pro Trp Arg Glu Leu Phe Ala Pro Lys Gly Ala Asp Gly Arg Thr Phe
                245                 250                 255

Glu Lys Phe Val Ala Glu Ser Gly Gly Ala Glu Ala Ile Trp Tyr Pro
            260                 265                 270

Phe Thr Glu Lys Pro Trp Met Lys Val Trp Thr Val Ser Pro Thr Lys
        275                 280                 285

Pro Asp Ser Ser Asn Glu Val Gly Ser Leu Gly Ser Ala Gly Ser Leu
290                 295                 300

Val Gly Lys Pro Pro Gln Ala Arg Glu Val Ser Gly Pro Tyr Asn Tyr
305                 310                 315                 320

Ile Phe Ser Asp Asn Leu Pro Glu Pro Ile Thr Asp Met Ile Gly Ala
                325                 330                 335

Ile Asn Ala Gly Asn Pro Gly Ile Ala Pro Leu Phe Gly Pro Ala Met
            340                 345                 350

Tyr Glu Ile Thr Lys Leu Gly Leu Ala Ala Thr Asn Ala Asn Asp Ile
        355                 360                 365

Trp Gly Trp Ser Lys Asp Val Gln Phe Tyr Ile Lys Ala Thr Thr Leu
370                 375                 380

Arg Leu Thr Glu Gly Gly Gly Ala Val Val Thr Ser Arg Ala Asn Ile
385                 390                 395                 400

Ala Thr Val Ile Asn Asp Phe Thr Glu Trp Phe His Glu Arg Ile Glu
                405                 410                 415

Phe Tyr Arg Ala Lys Gly Glu Phe Pro Leu Asn Gly Pro Val Glu Ile
            420                 425                 430

Arg Cys Cys Gly Leu Asp Gln Ala Ala Asp Val Lys Val Pro Ser Val
        435                 440                 445

Gly Pro Pro Thr Ile Ser Ala Thr Arg Pro Arg Pro Asp His Pro Asp
450                 455                 460

Trp Asp Val Ala Ile Trp Leu Asn Val Leu Gly Val Pro Gly Thr Pro
465                 470                 475                 480

Gly Met Phe Glu Phe Tyr Arg Glu Met Glu Gln Trp Met Arg Ser His
                485                 490                 495

Tyr Asn Asn Asp Asp Ala Thr Phe Arg Pro Glu Trp Ser Lys Gly Trp
            500                 505                 510

Ala Phe Gly Pro Asp Pro Tyr Thr Asp Asn Asp Ile Val Thr Asn Lys
        515                 520                 525

Met Arg Ala Thr Tyr Ile Glu Gly Val Pro Thr Thr Glu Asn Trp Asp
530                 535                 540
```

Thr Ala Arg Ala Arg Tyr Asn Gln Ile Asp Pro His Arg Val Phe Thr
545                 550                 555                 560

Asn Gly Phe Met Asp Lys Leu Leu Pro
                565

(2) INFORMATION FOR SEQ ID NO: 24:

(i) SEQUENCE CHARACTERISTICS:
        (A) LENGTH: 1728 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 19..1728

(xi) SEQUENCE DESCRIPTION: SEQ ID NO: 24:

```
AATTTGGAGG GGAACATT ATG AGT AAT CAT CAC CAT GGG CAT GCC TCG ACC         51
                   Met Ser Asn His His His Gly His Ala Ser Thr
                   1               5                  10

GGG CCG GTC GCG CCG CTT CCG ACG CCG CCG AAC TTC CCG AAC GAC ATC         99
Gly Pro Val Ala Pro Leu Pro Thr Pro Pro Asn Phe Pro Asn Asp Ile
                15                  20                  25

GCG CTG TTC CAG CAG GCG TAC CAG AAC TGG TCC AAG GAG ATC ATG CTG        147
Ala Leu Phe Gln Gln Ala Tyr Gln Asn Trp Ser Lys Glu Ile Met Leu
            30                  35                  40

GAC GCC ACT TGG GTC TGC TCG CCC AAG ACG CCG CAG GAT GTC GTT CGC        195
Asp Ala Thr Trp Val Cys Ser Pro Lys Thr Pro Gln Asp Val Val Arg
        45                  50                  55

CTT GCC AAC TGG GCG CAC GAG CAC GAC TAC AAG ATC CGC CCG CGC GGC        243
Leu Ala Asn Trp Ala His Glu His Asp Tyr Lys Ile Arg Pro Arg Gly
    60                  65                  70                  75

GCG ATG CAC GGC TGG ACC CCG CTC ACC GTG GAG AAG GGG GCC AAC GTC        291
Ala Met His Gly Trp Thr Pro Leu Thr Val Glu Lys Gly Ala Asn Val
                80                  85                  90

GAG AAG GTG ATC CTC GCC GAC ACG ATG ACG CAT CTG AAC GGC ATC ACG        339
Glu Lys Val Ile Leu Ala Asp Thr Met Thr His Leu Asn Gly Ile Thr
            95                 100                 105

GTG AAC ACG GGC GGC CCC GTG GCT ACC GTC ACC GCC GGT GCC GGC GCC        387
Val Asn Thr Gly Gly Pro Val Ala Thr Val Thr Ala Gly Ala Gly Ala
        110                 115                 120

AGC ATC GAG GCG ATC GTC ACC GAA CTG CAG AAG CAC GAC CTC GGC TGG        435
Ser Ile Glu Ala Ile Val Thr Glu Leu Gln Lys His Asp Leu Gly Trp
    125                 130                 135

GCC AAC CTG CCC GCT CCG GGT GTG CTG TCG ATC GGT GGC GCC CTT GCG        483
Ala Asn Leu Pro Ala Pro Gly Val Leu Ser Ile Gly Gly Ala Leu Ala
140                 145                 150                 155

GTC AAC GCG CAC GGT GCG GCG CTG CCG GCC GTC GGC CAG ACC ACG CTG        531
Val Asn Ala His Gly Ala Ala Leu Pro Ala Val Gly Gln Thr Thr Leu
                160                 165                 170

CCC GGT CAC ACC TAC GGT TCG CTG AGC AAC CTG GTC ACC GAG CTG ACC        579
Pro Gly His Thr Tyr Gly Ser Leu Ser Asn Leu Val Thr Glu Leu Thr
            175                 180                 185

GCG GTC GTC TGG AAC GGC ACC ACC TAC GCA CTC GAG ACG TAC CAG CGC        627
Ala Val Val Trp Asn Gly Thr Thr Tyr Ala Leu Glu Thr Tyr Gln Arg
        190                 195                 200

AAC GAT CCT CGG ATC ACC CCA CTG CTC ACC AAC CTC GGG CGC TGC TTC        675
Asn Asp Pro Arg Ile Thr Pro Leu Leu Thr Asn Leu Gly Arg Cys Phe
    205                 210                 215

CTG ACC TCG GTG ACG ATG CAG GCC GGC CCC AAC TTC CGT CAG CGG TGC        723
Leu Thr Ser Val Thr Met Gln Ala Gly Pro Asn Phe Arg Gln Arg Cys
```

```
                220                 225                 230                 235
CAG AGC TAC ACC GAC ATC CCG TGG CGG GAA CTG TTC GCG CCG AAG GGC     771
Gln Ser Tyr Thr Asp Ile Pro Trp Arg Glu Leu Phe Ala Pro Lys Gly
                240                 245                 250

GCC GAC GGC CGC ACG TTC GAG AAG TTC GTC GCG GAA TCG GGC GGC GCC     819
Ala Asp Gly Arg Thr Phe Glu Lys Phe Val Ala Glu Ser Gly Gly Ala
                255                 260                 265

GAG GCG ATC TGG TAC CCG TTC ACC GAG AAG CCG TGG ATG AAG GTG TGG     867
Glu Ala Ile Trp Tyr Pro Phe Thr Glu Lys Pro Trp Met Lys Val Trp
                270                 275                 280

ACG GTC TCG CCG ACC AAG CCG GAC TCG TCG AAC GAG GTC GGA AGC CTC     915
Thr Val Ser Pro Thr Lys Pro Asp Ser Ser Asn Glu Val Gly Ser Leu
            285                 290                 295

GGC TCG GCG GGC TCC CTC GTC GGC AAG CCT CCG CAG GCG CGT GAG GTC     963
Gly Ser Ala Gly Ser Leu Val Gly Lys Pro Pro Gln Ala Arg Glu Val
300                 305                 310                 315

TCC GGC CCG TAC AAC TAC ATC TTC TCC GAC AAC CTG CCG GAG CCC ATC    1011
Ser Gly Pro Tyr Asn Tyr Ile Phe Ser Asp Asn Leu Pro Glu Pro Ile
                320                 325                 330

ACC GAC ATG ATC GGC GCC ATC AAC GCC GGA AAC CCC GGA ATC GCA CCG    1059
Thr Asp Met Ile Gly Ala Ile Asn Ala Gly Asn Pro Gly Ile Ala Pro
                335                 340                 345

CTG TTC GGC CCG GCG ATG TAC GAG ATC ACC AAG CTC GGG CTG GCC GCG    1107
Leu Phe Gly Pro Ala Met Tyr Glu Ile Thr Lys Leu Gly Leu Ala Ala
            350                 355                 360

ACG AAT GCC AAC GAC ATC TGG GGC TGG TCG AAG GAC GTC CAG TTC TAC    1155
Thr Asn Ala Asn Asp Ile Trp Gly Trp Ser Lys Asp Val Gln Phe Tyr
            365                 370                 375

ATC AAG GCC ACG ACG TTG CGA CTC ACC GAG GGC GGC GGC GCC GTC GTC    1203
Ile Lys Ala Thr Thr Leu Arg Leu Thr Glu Gly Gly Gly Ala Val Val
380                 385                 390                 395

ACG AGC CGC GCC AAC ATC GCG ACC GTG ATC AAC GAC TTC ACC GAG TGG    1251
Thr Ser Arg Ala Asn Ile Ala Thr Val Ile Asn Asp Phe Thr Glu Trp
                400                 405                 410

TTC CAC GAG CGC ATC GAG TTC TAC CGC GCG AAG GGC GAG TTC CCG CTC    1299
Phe His Glu Arg Ile Glu Phe Tyr Arg Ala Lys Gly Glu Phe Pro Leu
            415                 420                 425

AAC GGT CCG GTC GAG ATC CGC TGC TGC GGG CTC GAT CAG GCA GCC GAC    1347
Asn Gly Pro Val Glu Ile Arg Cys Cys Gly Leu Asp Gln Ala Ala Asp
            430                 435                 440

GTC AAG GTG CCG TCG GTG GGC CCG CCG ACC ATC TCG GCG ACC CGT CCG    1395
Val Lys Val Pro Ser Val Gly Pro Pro Thr Ile Ser Ala Thr Arg Pro
        445                 450                 455

CGT CCG GAT CAT CCG GAC TGG GAC GTC GCG ATC TGG CTG AAC GTT CTC    1443
Arg Pro Asp His Pro Asp Trp Asp Val Ala Ile Trp Leu Asn Val Leu
460                 465                 470                 475

GGT GTT CCG GGC ACC CCC GGC ATG TTC GAG TTC TAC CGC GAG ATG GAG    1491
Gly Val Pro Gly Thr Pro Gly Met Phe Glu Phe Tyr Arg Glu Met Glu
                480                 485                 490

CAG TGG ATG CGG AGC CAC TAC AAC AAC GAC GAC GCC ACC TTC CGG CCC    1539
Gln Trp Met Arg Ser His Tyr Asn Asn Asp Asp Ala Thr Phe Arg Pro
            495                 500                 505

GAG TGG TCG AAG GGG TGG GCG TTC GGT CCC GAC CCG TAC ACC GAC AAC    1587
Glu Trp Ser Lys Gly Trp Ala Phe Gly Pro Asp Pro Tyr Thr Asp Asn
            510                 515                 520

GAC ATC GTC ACG AAC AAG ATG CGC GCC ACC TAC ATC GAA GGT GTC CCG    1635
Asp Ile Val Thr Asn Lys Met Arg Ala Thr Tyr Ile Glu Gly Val Pro
            525                 530                 535

ACG ACC GAG AAC TGG GAC ACC GCG CGC GCT CGG TAC AAC CAG ATC GAC    1683
Thr Thr Glu Asn Trp Asp Thr Ala Arg Ala Arg Tyr Asn Gln Ile Asp
```

```
                540                545                550                555
CCG CAT CGC GTG TTC ACC AAC GGA TTC ATG GAC AAG CTG CTT CCG             1728
Pro His Arg Val Phe Thr Asn Gly Phe Met Asp Lys Leu Leu Pro
                560                565                570
```

(2) INFORMATION FOR SEQ ID NO: 25:

(i) SEQUENCE CHARACTERISTICS:
        (A) LENGTH: 570 amino acids
        (B) TYPE: amino acid
        (D) TOPOLOGY: linear (ii) MOLECULE TYPE: Protein (xi) SEQUENCE DESCRIPTION: SEQ ID NO: 25:

```
Met Ser Asn His His His Gly His Ala Ser Thr Gly Pro Val Ala Pro
 1               5                  10                  15

Leu Pro Thr Pro Pro Asn Phe Pro Asn Asp Ile Ala Leu Phe Gln Gln
                20                  25                  30

Ala Tyr Gln Asn Trp Ser Lys Glu Ile Met Leu Asp Ala Thr Trp Val
            35                  40                  45

Cys Ser Pro Lys Thr Pro Gln Asp Val Val Arg Leu Ala Asn Trp Ala
        50                  55                  60

His Glu His Asp Tyr Lys Ile Arg Pro Arg Gly Ala Met His Gly Trp
 65                 70                  75                  80

Thr Pro Leu Thr Val Glu Lys Gly Ala Asn Val Glu Lys Val Ile Leu
                85                  90                  95

Ala Asp Thr Met Thr His Leu Asn Gly Ile Thr Val Asn Thr Gly Gly
                100                 105                 110

Pro Val Ala Thr Val Thr Ala Gly Ala Gly Ala Ser Ile Glu Ala Ile
            115                 120                 125

Val Thr Glu Leu Gln Lys His Asp Leu Gly Trp Ala Asn Leu Pro Ala
130                 135                 140

Pro Gly Val Leu Ser Ile Gly Gly Ala Leu Ala Val Asn Ala His Gly
145                 150                 155                 160

Ala Ala Leu Pro Ala Val Gly Gln Thr Thr Leu Pro Gly His Thr Tyr
                165                 170                 175

Gly Ser Leu Ser Asn Leu Val Thr Glu Leu Thr Ala Val Val Trp Asn
            180                 185                 190

Gly Thr Thr Tyr Ala Leu Glu Thr Tyr Gln Arg Asn Asp Pro Arg Ile
        195                 200                 205

Thr Pro Leu Leu Thr Asn Leu Gly Arg Cys Phe Leu Thr Ser Val Thr
210                 215                 220

Met Gln Ala Gly Pro Asn Phe Arg Gln Arg Cys Gln Ser Tyr Thr Asp
225                 230                 235                 240

Ile Pro Trp Arg Glu Leu Phe Ala Pro Lys Gly Ala Asp Gly Arg Thr
                245                 250                 255

Phe Glu Lys Phe Val Ala Glu Ser Gly Gly Ala Glu Ala Ile Trp Tyr
            260                 265                 270

Pro Phe Thr Glu Lys Pro Trp Met Lys Val Trp Thr Val Ser Pro Thr
        275                 280                 285

Lys Pro Asp Ser Ser Asn Glu Val Gly Ser Leu Gly Ser Ala Gly Ser
290                 295                 300

Leu Val Gly Lys Pro Pro Gln Ala Arg Glu Val Ser Gly Pro Tyr Asn
305                 310                 315                 320

Tyr Ile Phe Ser Asp Asn Leu Pro Glu Pro Ile Thr Asp Met Ile Gly
                325                 330                 335
```

```
Ala Ile Asn Ala Gly Asn Pro Gly Ile Ala Pro Leu Phe Gly Pro Ala
            340                 345                 350

Met Tyr Glu Ile Thr Lys Leu Gly Leu Ala Ala Thr Asn Ala Asn Asp
            355                 360                 365

Ile Trp Gly Trp Ser Lys Asp Val Gln Phe Tyr Ile Lys Ala Thr Thr
            370                 375                 380

Leu Arg Leu Thr Glu Gly Gly Ala Val Val Thr Ser Arg Ala Asn
385                 390                 395                 400

Ile Ala Thr Val Ile Asn Asp Phe Thr Glu Trp Phe His Glu Arg Ile
            405                 410                 415

Glu Phe Tyr Arg Ala Lys Gly Glu Phe Pro Leu Asn Gly Pro Val Glu
            420                 425                 430

Ile Arg Cys Cys Gly Leu Asp Gln Ala Ala Asp Val Lys Val Pro Ser
            435                 440                 445

Val Gly Pro Pro Thr Ile Ser Ala Thr Arg Pro Arg Pro Asp His Pro
            450                 455                 460

Asp Trp Asp Val Ala Ile Trp Leu Asn Val Leu Gly Val Pro Gly Thr
465                 470                 475                 480

Pro Gly Met Phe Glu Phe Tyr Arg Glu Met Glu Gln Trp Met Arg Ser
            485                 490                 495

His Tyr Asn Asn Asp Asp Ala Thr Phe Arg Pro Glu Trp Ser Lys Gly
            500                 505                 510

Trp Ala Phe Gly Pro Asp Pro Tyr Thr Asp Asn Asp Ile Val Thr Asn
            515                 520                 525

Lys Met Arg Ala Thr Tyr Ile Glu Gly Val Pro Thr Thr Glu Asn Trp
            530                 535                 540

Asp Thr Ala Arg Ala Arg Tyr Asn Gln Ile Asp Pro His Arg Val Phe
545                 550                 555                 560

Thr Asn Gly Phe Met Asp Lys Leu Leu Pro
            565                 570

(2) INFORMATION FOR SEQ ID NO: 26:

(i) SEQUENCE CHARACTERISTICS:
        (A) LENGTH: 1741 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..1741

(xi) SEQUENCE DESCRIPTION: SEQ ID NO: 26:

GAATTTAAGG GGAACATCG ATG AGT AAT ACG CGT AAA CGC AAG CGC CGT ACG        52
                    Met Ser Asn Thr Arg Lys Arg Lys Arg Arg Thr
                    1               5                  10

CAT GCC TCG ACC GGG CCG GTC GCG CCG CTT CCG ACG CCG CCG AAC TTC        100
His Ala Ser Thr Gly Pro Val Ala Pro Leu Pro Thr Pro Pro Asn Phe
                15                  20                  25

CCG AAC GAC ATC GCG CTG TTC CAG CAG GCG TAC CAG AAC TGG TCC AAG        148
Pro Asn Asp Ile Ala Leu Phe Gln Gln Ala Tyr Gln Asn Trp Ser Lys
            30                  35                  40

GAG ATC ATG CTG GAC GCC ACT TGG GTC TGC TCG CCC AAG ACG CCG CAG        196
Glu Ile Met Leu Asp Ala Thr Trp Val Cys Ser Pro Lys Thr Pro Gln
        45                  50                  55

GAT GTC GTT CGC CTT GCC AAC TGG GCG CAC GAG CAC GAC TAC AAG ATC        244
Asp Val Val Arg Leu Ala Asn Trp Ala His Glu His Asp Tyr Lys Ile
60                  65                  70                  75
```

```
CGC CCG CGC GGC GCG ATG CAC GGC TGG ACC CCG CTC ACC GTG GAG AAG        292
Arg Pro Arg Gly Ala Met His Gly Trp Thr Pro Leu Thr Val Glu Lys
                80                  85                  90

GGG GCC AAC GTC GAG AAG GTG ATC CTC GCC GAC ACG ATG ACG CAT CTG        340
Gly Ala Asn Val Glu Lys Val Ile Leu Ala Asp Thr Met Thr His Leu
                95                  100                 105

AAC GGC ATC ACG GTG AAC ACG GGC GGC CCC GTG GCT ACC GTC ACC GCC        388
Asn Gly Ile Thr Val Asn Thr Gly Gly Pro Val Ala Thr Val Thr Ala
                110                 115                 120

GGT GCC GGC GCC AGC ATC GAG GCG ATC GTC ACC GAA CTG CAG AAG CAC        436
Gly Ala Gly Ala Ser Ile Glu Ala Ile Val Thr Glu Leu Gln Lys His
            125                 130                 135

GAC CTC GGC TGG GCC AAC CTG CCC GCT CCG GGT GTG CTG TCG ATC GGT        484
Asp Leu Gly Trp Ala Asn Leu Pro Ala Pro Gly Val Leu Ser Ile Gly
140                 145                 150                 155

GGC GCC CTT GCG GTC AAC GCG CAC GGT GCG GCG CTG CCG GCC GTC GGC        532
Gly Ala Leu Ala Val Asn Ala His Gly Ala Ala Leu Pro Ala Val Gly
                160                 165                 170

CAG ACC ACG CTG CCC GGT CAC ACC TAC GGT TCG CTG AGC AAC CTG GTC        580
Gln Thr Thr Leu Pro Gly His Thr Tyr Gly Ser Leu Ser Asn Leu Val
            175                 180                 185

ACC GAG CTG ACC GCG GTC GTC TGG AAC GGC ACC ACC TAC GCA CTC GAG        628
Thr Glu Leu Thr Ala Val Val Trp Asn Gly Thr Thr Tyr Ala Leu Glu
            190                 195                 200

ACG TAC CAG CGC AAC GAT CCT CGG ATC ACC CCA CTG CTC ACC AAC CTC        676
Thr Tyr Gln Arg Asn Asp Pro Arg Ile Thr Pro Leu Leu Thr Asn Leu
    205                 210                 215

GGG CGC TGC TTC CTG ACC TCG GTG ACG ATG CAG GCC GGC CCC AAC TTC        724
Gly Arg Cys Phe Leu Thr Ser Val Thr Met Gln Ala Gly Pro Asn Phe
220                 225                 230                 235

CGT CAG CGG TGC CAG AGC TAC ACC GAC ATC CCG TGG CGG GAA CTG TTC        772
Arg Gln Arg Cys Gln Ser Tyr Thr Asp Ile Pro Trp Arg Glu Leu Phe
                240                 245                 250

GCG CCG AAG GGC GCC GAC GGC CGC ACG TTC GAG AAG TTC GTC GCG GAA        820
Ala Pro Lys Gly Ala Asp Gly Arg Thr Phe Glu Lys Phe Val Ala Glu
            255                 260                 265

TCG GGC GGC GCC GAG GCG ATC TGG TAC CCG TTC ACC GAG AAG CCG TGG        868
Ser Gly Gly Ala Glu Ala Ile Trp Tyr Pro Phe Thr Glu Lys Pro Trp
        270                 275                 280

ATG AAG GTG TGG ACG GTC TCG CCG ACC AAG CCG GAC TCG TCG AAC GAG        916
Met Lys Val Trp Thr Val Ser Pro Thr Lys Pro Asp Ser Ser Asn Glu
285                 290                 295

GTC GGA AGC CTC GGC TCG GCG GGC TCC CTC GTC GGC AAG CCT CCG CAG        964
Val Gly Ser Leu Gly Ser Ala Gly Ser Leu Val Gly Lys Pro Pro Gln
300                 305                 310                 315

GCG CGT GAG GTC TCC GGC CCG TAC AAC TAC ATC TTC TCC GAC AAC CTG       1012
Ala Arg Glu Val Ser Gly Pro Tyr Asn Tyr Ile Phe Ser Asp Asn Leu
                320                 325                 330

CCG GAG CCC ATC ACC GAC ATG ATC GGC GCC ATC AAC GCC GGA AAC CCC       1060
Pro Glu Pro Ile Thr Asp Met Ile Gly Ala Ile Asn Ala Gly Asn Pro
            335                 340                 345

GGA ATC GCA CCG CTG TTC GGC CCG GCG ATG TAC GAG ATC ACC AAG CTC       1108
Gly Ile Ala Pro Leu Phe Gly Pro Ala Met Tyr Glu Ile Thr Lys Leu
        350                 355                 360

GGG CTG GCC GCG ACG AAT GCC AAC GAC ATC TGG GGC TGG TCG AAG GAC       1156
Gly Leu Ala Ala Thr Asn Ala Asn Asp Ile Trp Gly Trp Ser Lys Asp
365                 370                 375

GTC CAG TTC TAC ATC AAG GCC ACG ACG TTG CGA CTC ACC GAG GGC GGC       1204
Val Gln Phe Tyr Ile Lys Ala Thr Thr Leu Arg Leu Thr Glu Gly Gly
380                 385                 390                 395
```

-continued

```
GGC GCC GTC GTC ACG AGC CGC GCC AAC ATC GCG ACC GTG ATC AAC GAC      1252
Gly Ala Val Val Thr Ser Arg Ala Asn Ile Ala Thr Val Ile Asn Asp
                400                 405                 410

TTC ACC GAG TGG TTC CAC GAG CGC ATC GAG TTC TAC CGC GCG AAG GGC      1300
Phe Thr Glu Trp Phe His Glu Arg Ile Glu Phe Tyr Arg Ala Lys Gly
                415                 420                 425

GAG TTC CCG CTC AAC GGT CCG GTC GAG ATC CGC TGC TGC GGG CTC GAT      1348
Glu Phe Pro Leu Asn Gly Pro Val Glu Ile Arg Cys Cys Gly Leu Asp
                430                 435                 440

CAG GCA GCC GAC GTC AAG GTG CCG TCG GTG GGC CCG CCG ACC ATC TCG      1396
Gln Ala Ala Asp Val Lys Val Pro Ser Val Gly Pro Pro Thr Ile Ser
                445                 450                 455

GCG ACC CGT CCG CGT CCG GAT CAT CCG GAC TGG GAC GTC GCG ATC TGG      1444
Ala Thr Arg Pro Arg Pro Asp His Pro Asp Trp Asp Val Ala Ile Trp
460                 465                 470                 475

CTG AAC GTT CTC GGT GTT CCG GGC ACC CCC GGC ATG TTC GAG TTC TAC      1492
Leu Asn Val Leu Gly Val Pro Gly Thr Pro Gly Met Phe Glu Phe Tyr
                480                 485                 490

CGC GAG ATG GAG CAG TGG ATG CGG AGC CAC TAC AAC AAC GAC GAC GCC      1540
Arg Glu Met Glu Gln Trp Met Arg Ser His Tyr Asn Asn Asp Asp Ala
                495                 500                 505

ACC TTC CGG CCC GAG TGG TCG AAG GGG TGG GCG TTC GGT CCC GAC CCG      1588
Thr Phe Arg Pro Glu Trp Ser Lys Gly Trp Ala Phe Gly Pro Asp Pro
                510                 515                 520

TAC ACC GAC AAC GAC ATC GTC ACG AAC AAG ATG CGC GCC ACC TAC ATC      1636
Tyr Thr Asp Asn Asp Ile Val Thr Asn Lys Met Arg Ala Thr Tyr Ile
                525                 530                 535

GAA GGT GTC CCG ACG ACC GAG AAC TGG GAC ACC GCG CGC GCT CGG TAC      1684
Glu Gly Val Pro Thr Thr Glu Asn Trp Asp Thr Ala Arg Ala Arg Tyr
540                 545                 550                 555

AAC CAG ATC GAC CCG CAT CGC GTG TTC ACC AAC GGA TTC ATG GAC AAG      1732
Asn Gln Ile Asp Pro His Arg Val Phe Thr Asn Gly Phe Met Asp Lys
                560                 565                 570

CTG CTT CCG                                                          1741
Leu Leu Pro
```

(2) INFORMATION FOR SEQ ID NO: 27:

(i) SEQUENCE CHARACTERISTICS:
        (A) LENGTH: 574 amino acids
        (B) TYPE: amino acid
        (D) TOPOLOGY: linear (ii) MOLECULE TYPE: Protein (xi) SEQUENCE DESCRIPTION: SEQ ID NO: 27:

```
Met Ser Asn Thr Arg Lys Arg Lys Arg Arg Thr His Ala Ser Thr Gly
1               5                   10                  15

Pro Val Ala Pro Leu Pro Thr Pro Pro Asn Phe Pro Asn Asp Ile Ala
                20                  25                  30

Leu Phe Gln Gln Ala Tyr Gln Asn Trp Ser Lys Glu Ile Met Leu Asp
            35                  40                  45

Ala Thr Trp Val Cys Ser Pro Lys Thr Pro Gln Asp Val Val Arg Leu
        50                  55                  60

Ala Asn Trp Ala His Glu His Asp Tyr Lys Ile Arg Pro Arg Gly Ala
65                  70                  75                  80

Met His Gly Trp Thr Pro Leu Thr Val Glu Lys Gly Ala Asn Val Glu
                85                  90                  95

Lys Val Ile Leu Ala Asp Thr Met Thr His Leu Asn Gly Ile Thr Val
                100                 105                 110
```

-continued

```
Asn Thr Gly Gly Pro Val Ala Thr Val Thr Ala Gly Ala Gly Ala Ser
            115                 120                 125
Ile Glu Ala Ile Val Thr Glu Leu Gln Lys His Asp Leu Gly Trp Ala
130                 135                 140
Asn Leu Pro Ala Pro Gly Val Leu Ser Ile Gly Gly Ala Leu Ala Val
145                 150                 155                 160
Asn Ala His Gly Ala Ala Leu Pro Ala Val Gly Gln Thr Thr Leu Pro
                165                 170                 175
Gly His Thr Tyr Gly Ser Leu Ser Asn Leu Val Thr Glu Leu Thr Ala
            180                 185                 190
Val Val Trp Asn Gly Thr Thr Tyr Ala Leu Glu Thr Tyr Gln Arg Asn
            195                 200                 205
Asp Pro Arg Ile Thr Pro Leu Leu Thr Asn Leu Gly Arg Cys Phe Leu
210                 215                 220
Thr Ser Val Thr Met Gln Ala Gly Pro Asn Phe Arg Gln Arg Cys Gln
225                 230                 235                 240
Ser Tyr Thr Asp Ile Pro Trp Arg Glu Leu Phe Ala Pro Lys Gly Ala
                245                 250                 255
Asp Gly Arg Thr Phe Glu Lys Phe Val Ala Glu Ser Gly Gly Ala Glu
            260                 265                 270
Ala Ile Trp Tyr Pro Phe Thr Glu Lys Pro Trp Met Lys Val Trp Thr
            275                 280                 285
Val Ser Pro Thr Lys Pro Asp Ser Ser Asn Glu Val Gly Ser Leu Gly
290                 295                 300
Ser Ala Gly Ser Leu Val Gly Lys Pro Pro Gln Ala Arg Glu Val Ser
305                 310                 315                 320
Gly Pro Tyr Asn Tyr Ile Phe Ser Asp Asn Leu Pro Glu Pro Ile Thr
                325                 330                 335
Asp Met Ile Gly Ala Ile Asn Ala Gly Asn Pro Gly Ile Ala Pro Leu
            340                 345                 350
Phe Gly Pro Ala Met Tyr Glu Ile Thr Lys Leu Gly Leu Ala Ala Thr
            355                 360                 365
Asn Ala Asn Asp Ile Trp Gly Trp Ser Lys Asp Val Gln Phe Tyr Ile
370                 375                 380
Lys Ala Thr Thr Leu Arg Leu Thr Glu Gly Gly Ala Val Val Thr
385                 390                 395                 400
Ser Arg Ala Asn Ile Ala Thr Val Ile Asn Asp Phe Thr Glu Trp Phe
                405                 410                 415
His Glu Arg Ile Glu Phe Tyr Arg Ala Lys Gly Glu Phe Pro Leu Asn
            420                 425                 430
Gly Pro Val Glu Ile Arg Cys Cys Gly Leu Asp Gln Ala Ala Asp Val
            435                 440                 445
Lys Val Pro Ser Val Gly Pro Thr Ile Ser Ala Thr Arg Pro Arg
450                 455                 460
Pro Asp His Pro Asp Trp Asp Val Ala Ile Trp Leu Asn Val Leu Gly
465                 470                 475                 480
Val Pro Gly Thr Pro Gly Met Phe Glu Phe Tyr Arg Glu Met Glu Gln
                485                 490                 495
Trp Met Arg Ser His Tyr Asn Asn Asp Ala Thr Phe Arg Pro Glu
            500                 505                 510
Trp Ser Lys Gly Trp Ala Phe Gly Pro Asp Pro Tyr Thr Asp Asn Asp
            515                 520                 525
Ile Val Thr Asn Lys Met Arg Ala Thr Tyr Ile Glu Gly Val Pro Thr
```

```
                530              535              540
Thr Glu Asn Trp Asp Thr Ala Arg Ala Arg Tyr Asn Gln Ile Asp Pro
545                  550                  555                  560

His Arg Val Phe Thr Asn Gly Phe Met Asp Lys Leu Leu Pro
                565                 570
```

(2) INFORMATION FOR SEQ ID NO: 28:

(i) SEQUENCE CHARACTERISTICS:
        (A) LENGTH: 1731 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 25..1731

(xi) SEQUENCE DESCRIPTION: SEQ ID NO: 28:

```
GAATTCACAC AGGAAACAGA ATTC ATG GTT ATG CAC CAT GGG CAT GCC TCG          51
                          Met Val Met His His Gly His Ala Ser
                           1               5

ACC GGG CCG GTC GCG CCG CTT CCG ACG CCG CCG AAC TTC CCG AAC GAC          99
Thr Gly Pro Val Ala Pro Leu Pro Thr Pro Pro Asn Phe Pro Asn Asp
 10              15                  20                  25

ATC GCG CTG TTC CAG CAG GCG TAC CAG AAC TGG TCC AAG GAG ATC ATG         147
Ile Ala Leu Phe Gln Gln Ala Tyr Gln Asn Trp Ser Lys Glu Ile Met
                 30                  35                  40

CTG GAC GCC ACT TGG GTC TGC TCG CCC AAG ACG CCG CAG GAT GTC GTT         195
Leu Asp Ala Thr Trp Val Cys Ser Pro Lys Thr Pro Gln Asp Val Val
             45                  50                  55

CGC CTT GCC AAC TGG GCG CAC GAG CAC GAC TAC AAG ATC CGC CCG CGC         243
Arg Leu Ala Asn Trp Ala His Glu His Asp Tyr Lys Ile Arg Pro Arg
         60                  65                  70

GGC GCG ATG CAC GGC TGG ACC CCG CTC ACC GTG GAG AAG GGG GCC AAC         291
Gly Ala Met His Gly Trp Thr Pro Leu Thr Val Glu Lys Gly Ala Asn
     75                  80                  85

GTC GAG AAG GTG ATC CTC GCC GAC ACG ATG ACG CAT CTG AAC GGC ATC         339
Val Glu Lys Val Ile Leu Ala Asp Thr Met Thr His Leu Asn Gly Ile
 90                  95                 100                 105

ACG GTG AAC ACG GGC GGC CCC GTG GCT ACC GTC ACC GCC GGT GCC GGC         387
Thr Val Asn Thr Gly Gly Pro Val Ala Thr Val Thr Ala Gly Ala Gly
                110                 115                 120

GCC AGC ATC GAG GCG ATC GTC ACC GAA CTG CAG AAG CAC GAC CTC GGC         435
Ala Ser Ile Glu Ala Ile Val Thr Glu Leu Gln Lys His Asp Leu Gly
            125                 130                 135

TGG GCC AAC CTG CCC GCT CCG GGT GTG CTG TCG ATC GGT GGC GCC CTT         483
Trp Ala Asn Leu Pro Ala Pro Gly Val Leu Ser Ile Gly Gly Ala Leu
        140                 145                 150

GCG GTC AAC GCG CAC GGT GCG GCG CTG CCG GCC GTC GGC CAG ACC ACG         531
Ala Val Asn Ala His Gly Ala Ala Leu Pro Ala Val Gly Gln Thr Thr
    155                 160                 165

CTG CCC GGT CAC ACC TAC GGT TCG CTG AGC AAC CTG GTC ACC GAG CTG         579
Leu Pro Gly His Thr Tyr Gly Ser Leu Ser Asn Leu Val Thr Glu Leu
170                 175                 180                 185

ACC GCG GTC GTC TGG AAC GGC ACC ACC TAC GCA CTC GAG ACG TAC CAG         627
Thr Ala Val Val Trp Asn Gly Thr Thr Tyr Ala Leu Glu Thr Tyr Gln
                190                 195                 200

CGC AAC GAT CCT CGG ATC ACC CCA CTG CTC ACC AAC CTC GGG CGC TGC         675
Arg Asn Asp Pro Arg Ile Thr Pro Leu Leu Thr Asn Leu Gly Arg Cys
            205                 210                 215

TTC CTG ACC TCG GTG ACG ATG CAG GCC GGC CCC AAC TTC CGT CAG CGG         723
```

```
Phe Leu Thr Ser Val Thr Met Gln Ala Gly Pro Asn Phe Arg Gln Arg
            220                 225                 230

TGC CAG AGC TAC ACC GAC ATC CCG TGG CGG GAA CTG TTC GCG CCG AAG       771
Cys Gln Ser Tyr Thr Asp Ile Pro Trp Arg Glu Leu Phe Ala Pro Lys
        235                 240                 245

GGC GCC GAC GGC CGC ACG TTC GAG AAG TTC GTC GCG GAA TCG GGC GGC       819
Gly Ala Asp Gly Arg Thr Phe Glu Lys Phe Val Ala Glu Ser Gly Gly
250                 255                 260                 265

GCC GAG GCG ATC TGG TAC CCG TTC ACC GAG AAG CCG TGG ATG AAG GTG       867
Ala Glu Ala Ile Trp Tyr Pro Phe Thr Glu Lys Pro Trp Met Lys Val
                    270                 275                 280

TGG ACG GTC TCG CCG ACC AAG CCG GAC TCG TCG AAC GAG GTC GGA AGC       915
Trp Thr Val Ser Pro Thr Lys Pro Asp Ser Ser Asn Glu Val Gly Ser
            285                 290                 295

CTC GGC TCG GCG GGC TCC CTC GTC GGC AAG CCT CCG CAG GCG CGT GAG       963
Leu Gly Ser Ala Gly Ser Leu Val Gly Lys Pro Pro Gln Ala Arg Glu
        300                 305                 310

GTC TCC GGC CCG TAC AAC TAC ATC TTC TCC GAC AAC CTG CCG GAG CCC      1011
Val Ser Gly Pro Tyr Asn Tyr Ile Phe Ser Asp Asn Leu Pro Glu Pro
315                 320                 325

ATC ACC GAC ATG ATC GGC GCC ATC AAC GCC GGA AAC CCC GGA ATC GCA      1059
Ile Thr Asp Met Ile Gly Ala Ile Asn Ala Gly Asn Pro Gly Ile Ala
330                 335                 340                 345

CCG CTG TTC GGC CCG GCG ATG TAC GAG ATC ACC AAG CTC GGG CTG GCC      1107
Pro Leu Phe Gly Pro Ala Met Tyr Glu Ile Thr Lys Leu Gly Leu Ala
                350                 355                 360

GCG ACG AAT GCC AAC GAC ATC TGG GGC TGG TCG AAG GAC GTC CAG TTC      1155
Ala Thr Asn Ala Asn Asp Ile Trp Gly Trp Ser Lys Asp Val Gln Phe
            365                 370                 375

TAC ATC AAG GCC ACG ACG TTG CGA CTC ACC GAG GGC GGC GGC GCC GTC      1203
Tyr Ile Lys Ala Thr Thr Leu Arg Leu Thr Glu Gly Gly Gly Ala Val
        380                 385                 390

GTC ACG AGC CGC GCC AAC ATC GCG ACC GTG ATC AAC GAC TTC ACC GAG      1251
Val Thr Ser Arg Ala Asn Ile Ala Thr Val Ile Asn Asp Phe Thr Glu
395                 400                 405

TGG TTC CAC GAG CGC ATC GAG TTC TAC CGC GCG AAG GGC GAG TTC CCG      1299
Trp Phe His Glu Arg Ile Glu Phe Tyr Arg Ala Lys Gly Glu Phe Pro
410                 415                 420                 425

CTC AAC GGT CCG GTC GAG ATC CGC TGC TGC GGG CTC GAT CAG GCA GCC      1347
Leu Asn Gly Pro Val Glu Ile Arg Cys Cys Gly Leu Asp Gln Ala Ala
                430                 435                 440

GAC GTC AAG GTG CCG TCG GTG GGC CCG CCG ACC ATC TCG GCG ACC CGT      1395
Asp Val Lys Val Pro Ser Val Gly Pro Pro Thr Ile Ser Ala Thr Arg
            445                 450                 455

CCG CGT CCG GAT CAT CCG GAC TGG GAC GTC GCG ATC TGG CTG AAC GTT      1443
Pro Arg Pro Asp His Pro Asp Trp Asp Val Ala Ile Trp Leu Asn Val
        460                 465                 470

CTC GGT GTT CCG GGC ACC CCC GGC ATG TTC GAG TTC TAC CGC GAG ATG      1491
Leu Gly Val Pro Gly Thr Pro Gly Met Phe Glu Phe Tyr Arg Glu Met
475                 480                 485

GAG CAG TGG ATG CGG AGC CAC TAC AAC AAC GAC GAC GCC ACC TTC CGG      1539
Glu Gln Trp Met Arg Ser His Tyr Asn Asn Asp Asp Ala Thr Phe Arg
490                 495                 500                 505

CCC GAG TGG TCG AAG GGG TGG GCG TTC GGT CCC GAC CCG TAC ACC GAC      1587
Pro Glu Trp Ser Lys Gly Trp Ala Phe Gly Pro Asp Pro Tyr Thr Asp
                510                 515                 520

AAC GAC ATC GTC ACG AAC AAG ATG CGC GCC ACC TAC ATC GAA GGT GTC      1635
Asn Asp Ile Val Thr Asn Lys Met Arg Ala Thr Tyr Ile Glu Gly Val
            525                 530                 535

CCG ACG ACC GAG AAC TGG GAC ACC GCG CGC GCT CGG TAC AAC CAG ATC      1683
```

```
Pro Thr Thr Glu Asn Trp Asp Thr Ala Arg Ala Arg Tyr Asn Gln Ile
         540                 545                 550

GAC CCG CAT CGC GTG TTC ACC AAC GGA TTC ATG GAC AAG CTG CTT CCG    1731
Asp Pro His Arg Val Phe Thr Asn Gly Phe Met Asp Lys Leu Leu Pro
    555                 560                 565
```

(2) INFORMATION FOR SEQ ID NO: 29:

(i) SEQUENCE CHARACTERISTICS:
        (A) LENGTH: 569 amino acids
        (B) TYPE: amino acid
        (D) TOPOLOGY: linear (ii) MOLECULE TYPE: Protein (xi) SEQUENCE DESCRIPTION: SEQ ID NO: 29:

```
Met Val Met His His Gly His Ala Ser Thr Gly Pro Val Ala Pro Leu
 1               5                  10                  15

Pro Thr Pro Pro Asn Phe Pro Asn Asp Ile Ala Leu Phe Gln Gln Ala
             20                  25                  30

Tyr Gln Asn Trp Ser Lys Glu Ile Met Leu Asp Ala Thr Trp Val Cys
         35                  40                  45

Ser Pro Lys Thr Pro Gln Asp Val Val Arg Leu Ala Asn Trp Ala His
     50                  55                  60

Glu His Asp Tyr Lys Ile Arg Pro Arg Gly Ala Met His Gly Trp Thr
 65                  70                  75                  80

Pro Leu Thr Val Glu Lys Gly Ala Asn Val Glu Lys Val Ile Leu Ala
                 85                  90                  95

Asp Thr Met Thr His Leu Asn Gly Ile Thr Val Asn Thr Gly Gly Pro
             100                 105                 110

Val Ala Thr Val Thr Ala Gly Ala Gly Ala Ser Ile Glu Ala Ile Val
            115                 120                 125

Thr Glu Leu Gln Lys His Asp Leu Gly Trp Ala Asn Leu Pro Ala Pro
        130                 135                 140

Gly Val Leu Ser Ile Gly Gly Ala Leu Ala Val Asn Ala His Gly Ala
145                 150                 155                 160

Ala Leu Pro Ala Val Gly Gln Thr Thr Leu Pro Gly His Thr Tyr Gly
                165                 170                 175

Ser Leu Ser Asn Leu Val Thr Glu Leu Thr Ala Val Val Trp Asn Gly
            180                 185                 190

Thr Thr Tyr Ala Leu Glu Thr Tyr Gln Arg Asn Asp Pro Arg Ile Thr
        195                 200                 205

Pro Leu Leu Thr Asn Leu Gly Arg Cys Phe Leu Thr Ser Val Thr Met
    210                 215                 220

Gln Ala Gly Pro Asn Phe Arg Gln Arg Cys Gln Ser Tyr Thr Asp Ile
225                 230                 235                 240

Pro Trp Arg Glu Leu Phe Ala Pro Lys Gly Ala Asp Gly Arg Thr Phe
                245                 250                 255

Glu Lys Phe Val Ala Glu Ser Gly Gly Ala Glu Ala Ile Trp Tyr Pro
            260                 265                 270

Phe Thr Glu Lys Pro Trp Met Lys Val Trp Thr Val Ser Pro Thr Lys
        275                 280                 285

Pro Asp Ser Ser Asn Glu Val Gly Ser Leu Gly Ser Ala Gly Ser Leu
    290                 295                 300

Val Gly Lys Pro Pro Gln Ala Arg Glu Val Ser Gly Pro Tyr Asn Tyr
305                 310                 315                 320

Ile Phe Ser Asp Asn Leu Pro Glu Pro Ile Thr Asp Met Ile Gly Ala
```

```
                        325                 330                 335
Ile Asn Ala Gly Asn Pro Gly Ile Ala Pro Leu Phe Gly Pro Ala Met
                340                 345                 350
Tyr Glu Ile Thr Lys Leu Gly Leu Ala Ala Thr Asn Ala Asn Asp Ile
                355                 360                 365
Trp Gly Trp Ser Lys Asp Val Gln Phe Tyr Ile Lys Ala Thr Thr Leu
            370                 375                 380
Arg Leu Thr Glu Gly Gly Ala Val Val Thr Ser Arg Ala Asn Ile
385                 390                 395                 400
Ala Thr Val Ile Asn Asp Phe Thr Glu Trp Phe His Glu Arg Ile Glu
                405                 410                 415
Phe Tyr Arg Ala Lys Gly Glu Phe Pro Leu Asn Gly Pro Val Glu Ile
                420                 425                 430
Arg Cys Cys Gly Leu Asp Gln Ala Ala Asp Val Lys Val Pro Ser Val
                435                 440                 445
Gly Pro Pro Thr Ile Ser Ala Thr Arg Pro Arg Pro Asp His Pro Asp
            450                 455                 460
Trp Asp Val Ala Ile Trp Leu Asn Val Leu Gly Val Pro Gly Thr Pro
465                 470                 475                 480
Gly Met Phe Glu Phe Tyr Arg Glu Met Glu Gln Trp Met Arg Ser His
                485                 490                 495
Tyr Asn Asn Asp Asp Ala Thr Phe Arg Pro Glu Trp Ser Lys Gly Trp
                500                 505                 510
Ala Phe Gly Pro Asp Pro Tyr Thr Asp Asn Asp Ile Val Thr Asn Lys
            515                 520                 525
Met Arg Ala Thr Tyr Ile Glu Gly Val Pro Thr Thr Glu Asn Trp Asp
            530                 535                 540
Thr Ala Arg Ala Arg Tyr Asn Gln Ile Asp Pro His Arg Val Phe Thr
545                 550                 555                 560
Asn Gly Phe Met Asp Lys Leu Leu Pro
                565
```

(2) INFORMATION FOR SEQ ID NO: 30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 30:

TCGCATGCCT CGACGGGCCC GGTGGCGCCG CTTCCG                        36

(2) INFORMATION FOR SEQ ID NO: 31:

(i) SEQUENCE CHARACTERISTICS:
        (A) LENGTH: 25 base pairs
        (B) TYPE: Nukleins
        (C) STRANDEDNESS: single
        (D) TOPOLOGY: linear (xi) SEQUENCE DESCRIPTION: SEQ ID NO: 31:

CGTGCTTCTG CAGTTCGGTG ACGAT                                  25

(2) INFORMATION FOR SEQ ID NO: 32:

(i) SEQUENCE CHARACTERISTICS:
        (A) LENGTH: 39 base pairs
        (B) TYPE: nucleic acid
        (C) STRANDEDNESS: single -continued

```
        (D) TOPOLOGY: linear (xi) SEQUENCE DESCRIPTION: SEQ ID NO: 32:

TCCCATGGCA CACAGGAAAC ATCGATGACC ATGATTACG                    39

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 33:

CGTGCTTCTG CAGTTCGGTG ACGAT                                   25

(2) INFORMATION FOR SEQ ID NO: 34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 34:

CGATGCACCA TGGGCATG                                           18
```

CHOLESTEROL OXIDASE FROM BREVIBACTERIUM STEROLICUM

The invention concerns a cholesterol oxidase from Brevibacterium sterolicum, a process for the production of a recombinant cholesterol oxidase from Brevibacterium sterolicum, a suitable DNA sequence for this process which results in a cytoplasmic expression of the recombinant cholesterol oxidase in the host bacterium as well as the recombinant cholesterol oxidase obtained in this manner.

Cholesterol oxidase is of major importance for the enzymatic determination of cholesterol. It catalyzes the oxidation of cholesterol to cholesten-3-one and $H_2O_2$. Cholesterol oxidase from various organisms such as Pseudomonas, Mycobacterium, Nocardia, Arthrobacter and Brevibacterium have already been described (T. Uwajima et al., Agr. Biol. Chem. 37 (1973), 2345–2350). All these known cholesterol oxidases are secreted proteins. The soil bacterium Brevibacterium sterolicum KY 3643 (ATCC 21387) has a particularly high activity of cholesterol oxidase. Three isoenzymes of cholesterol oxidase are known from this bacterium which differ in their isoelectric point, substrate specificity towards various steroids, affinity for cholesterol at the pH optimum and in their DNA and amino acid sequence (EP-A 0 452 112 and EP-A 560 983). Cholesterol oxidase I from Brevibacterium sterolicum has a low affinity for cholesterol ($K_M$ $1.1 \times 10^{-3}$ mol/l) and can only be obtained in a low yield from Brevibacterium sterolicum. It has already been attempted to express a complete DNA coding for cholesterol oxidase I in *E. coli*, but this has not yet succeeded (K. Fujishiro et al., Biochem. Biophys. Res. Com. 172 (1990), 721–727, T. Ohta et al., Gene 103 (1991), 93–96). The expression of special deletion mutants of the DNA coding for cholesterol oxidase I which were fused with parts of the lac z gene also did not lead to a satisfactory expression in *E. coli* (T. Ohta et al., Biosci. Biotech. Biochem. 56 (1992), 1786–1791). The cloning and expression of further cholesterol oxidases from Brevibacterium sterolicum is described in EP-A 0 452 112. However, expression of these DNAs likewise does not lead to an adequate amount of active cholesterol oxidase.

The object of the invention was to provide a cholesterol oxidase with a high affinity for cholesterol in large amounts and in an active form.

This object is achieved by a cholesterol oxidase which has the amino acid sequence shown in SEQ ID NO 2. This cholesterol oxidase is obtainable from Brevibacterium sterolicum or can also be produced by recombinant means.

It has surprisingly turned out that such a cholesterol oxidase can be produced recombinantly in a large amount and in an active form. This cholesterol oxidase has a molecular weight of 60 kD, an isoelectric point of ca. 5.5 (each measured in the Phast System, Pharmacia LKB) and a $K_M$ value for cholesterol of $1 \times 10^{-4}$ mol/l (in 0.5 mol/l potassium phosphate buffer pH 7.5 at 25° C.) and is active in a pH range of 5.5 to 8.0.

It has turned out that this cholesterol oxidase can be obtained in a large amount and in an active form when a DNA is used for a heterologous expression which codes for a peptide with cholesterol oxidase activity and is selected from the group
   a) the DNA sequence shown in SEQ ID NO 1 or the DNA sequence which is complementary thereto,
   b) DNA sequences which hybridize with the DNA sequence shown in SEQ ID NO 1 or with fragments of this DNA sequence,
   c) DNA sequences which, without degeneracy of the genetic code, would hybridize with the sequences defined in a) or b) and which code for a polypeptide with the same amino acid sequence,
wherein this DNA has one of the sequences shown in SEQ ID NO 3, 4 and/or 5. A DNA is preferably used which has the sequence shown in SEQ ID NO 1. However, it is also possible to replace degenerated codons by other codons that code for the same amino acid in a manner familiar to a person skilled in the art. Furthermore codons coding for additional amino acids can be added at the 5' end, at the 3' end or also within the sequence shown in SEQ ID NO 1 provided the DNA variants obtained in this way hybridize with the DNA sequence shown in SEQ ID NO 1 under the usual conditions (see T. Maniatis et al., Molecular Cloning, A Laboratory Manual, Cold Spring Harbor Laboratory, Cold Spring Harbor, N.Y. 1989). In addition the DNA used should have one of the sequences shown in SEQ ID NO 3, 4 and/or 5 and code for a peptide with cholesterol oxidase activity. A peptide with cholesterol oxidase activity is understood as a peptide which catalyzes the oxidation of cholesterol (5-cholesten-3-β-ol) to 4-cholesten-3-one and $H_2O_2$.

The invention therefore also concerns a DNA which codes for a peptide with cholesterol oxidase activity and is selected from the group
   a) the DNA sequence shown in SEQ ID NO 1 or the DNA sequence which is complementary thereto,
   b) DNA sequences which hybridize with the DNA sequence shown in SEQ ID NO 1 or with fragments of this DNA sequence,
   c) DNA sequences which, without degeneracy of the genetic code, would hybridize with the sequences defined in a) or b) and which code for a polypeptide with the same amino acid sequence,
wherein this DNA has one of the sequences shown in SEQ ID NO 3, 4 and/or 5.

With such a DNA it is possible to obtain an at least 10-fold higher activity of the recombinantly produced cholesterol oxidase in a crude extract than with the previously described processes and cholesterol oxidases.

The invention in addition concerns a process for the production of a recombinant cholesterol oxidase by transformation of a suitable host cell with a DNA according to the invention which is present in a suitable expression system, culturing the transformed host cells and isolating the cholesterol oxidase formed from the cytoplasm of the transformed cells.

With this process it is surprisingly possible to obtain a recombinant cholesterol oxidase in a large amount and in an active form from the cytoplasm of the transformed host cell. In this process the DNA used can contain an additional nucleotide sequence at the 5' end which has a translation start codon but no stop codon wherein this additional nucleotide sequence does not lead to a shift in the reading frame and does not represent a functionally active signal sequence for the secretion of the recombinant enzyme formed. The length of this nucleotide sequence is about 3 to 90 base pairs.

The additional nucleotide sequence preferably has one of the sequences shown in the sequence protocols 6, 8, 10, 12, 14 and 16 instead of the native signal sequence.

A preferred subject matter of the invention is therefore a process for the production of a recombinant cholesterol oxidase in which a DNA according to the invention is used which has one of the sequences shown in SEQ ID NO 6, 8, 10, 12, 14 or 16 at the 5' end.

The host cells used for the recombinant production are transformed according to known methods (see e.g. Sambrook, Fritsch and Maniatis, Molecular Cloning, A Laboratory Manual, Cold Spring Harbor Laboratory Press, Cold Spring Harbor 1989). The transformed host cells are then cultured under conditions which allow expression of the cholesterol oxidase gene. Depending on the expression vector used, it may be expedient in a well-known manner to add an inductor (e.g. lactose or isopropyl-β-D-thiogalacto-pyranoside (IPTG)) to the culture medium to increase the temperature or to limit the supply of glucose. Isolation of the recombinant cholesterol oxidase from the cytoplasm of the transformed cells is then achieved according to known methods.

With this process it is possible to obtained the cholesterol oxidase according to the invention as a recombinant enzyme in a yield of 8–20 U/ml. In contrast expression of the complete cholesterol oxidase gene which contains the signal sequence only results in a yield of less than 0.1 U/ml.

A preferred subject matter of the invention is a DNA according to the invention coding for a peptide with cholesterol oxidase activity which has one of the sequences shown in SEQ ID NO 6, 8, 10, 12, 14 and 16 at the 5' end. The sequences shown in the sequence protocols 18, 20, 22, 24, 26 and 28 are particularly preferred. These DNA sequences according to the invention are preferably present cloned in an expression vector. This DNA can be used to obtain the cholesterol oxidase according to the invention in any amount in bacteria that are conventionally used for the recombinant production of proteins. The expression is preferably carried out in E. coli.

The invention therefore also concerns a recombinant cholesterol oxidase which is coded by a DNA according to the invention and has one of the amino acid sequences shown in SEQ ID NO 7, 9, 11, 13, 15 or 17 at the N-terminal end.

This recombinant cholesterol oxidase is equally as suitable as the other cholesterol oxidases known from the state of the art for an enzymatic test for the determination of cholesterol. If necessary recognition sequences for specific proteases such as e.g. IgA protease, enterokinase or factor Xa can be integrated between these N-terminal sequences and the amino acid sequence of the mature cholesterol oxidase by in vitro mutagenesis in a manner familiar to a person skilled in the art so that even after cytoplasmic expression of a cholesterol oxidase extended by these N-terminal sequences it is possible to cleave off such fused N-terminal sequences.

A preferred subject matter of the invention is a recombinant cholesterol oxidase which has the amino acid sequence shown in SEQ ID NO 21, 23, 25, 27 or 29 as well as the use of such a recombinant cholesterol oxidase in an enzymatic test for the detection of cholesterol. In this process the $H_2O_2$ formed in the cholesterol oxidase reaction is preferably determined in a subsequent indicator reaction as a measure of the cholesterol present in the sample.

The plasmids pUC-chol-B2-BB (DSM 8274), pmgl-SphI (DSM 8272) and pfl-20AT1-SD (DSM 8273) mentioned in the examples were deposited on May 05, 1993 at the "Deutsche Sammlung fur Zellkulturen und Mikroorganismen GmbH", Mascheroder Weg 1b, D-3300 Braunschweig.

The application is elucidated in more detail by the following examples in conjunction with the sequence protocols and figures.

SEQ ID NO 1 shows the nucleic acid sequence of the cholesterol oxidase according to the invention.

SEQ ID NO 2 shows the amino acid sequence of the cholesterol oxidase according to the invention.

SEQ ID NOS 3–5 show nucleotide sequences from DNAs according to the invention coding for a peptide with cholesterol oxidase activity.

SEQ ID NOS 6–17 show the N-terminal sequences of recombinant cholesterol oxidase genes according to the invention (SEQ ID NOS 6, 8, 10, 12, 14 and 16) and the N-terminal amino acid sequences thereof (SEQ ID NOS 7, 9, 11, 13, 15 and 17). SEQ ID NOS 18–29 show the nucleic acid sequences and amino acid sequences thereof of cholesterol oxidases according to the invention.

They denote the following:

| Signal sequence | Complete sequence | Construct |
| --- | --- | --- |
| SEQ ID NO 6–7 | SEQ ID NO 18–19 | plac-Chol-cyt |
| SEQ ID NO 8–9 | SEQ ID NO 20–21 | ppfl-Chol-cyt |
| SEQ ID NO 10–11 | SEQ ID NO 22–23 | ppfl-MSN3H-Chol-cyt |
| SEQ ID NO 12–13 | SEQ ID NO 24–25 | ppfl-MSN4H-Chol-cyt |
| SEQ ID NO 14–15 | SEQ ID NO 26–27 | ppfl-MSN4R2K-Chol-cyt |
| SEQ ID NO 16–17 | SEQ ID NO 28–29 | ppfl-MVM3H-Chol-cyt |

SEQ ID NOS 30–33 show four oligonucleotides for amplification of a fragment of the cholesterol oxidase gene according to the invention.

SEQ ID NO 34 shows the sequence of an adapter oligonucleotide for the in vitro mutagenesis of the cholesterol oxidase gene according to example 5.

BRIEF DESCRIPTION OF THE DRAWINGS

FIG. 1 shows the plasmid pUC-Chol-B2-BB.

FIG. 2 shows the plasmid plac-Chol-cyt.

FIG. 3 shows the plasmid ppfl-Chol-cyt.

FIG. 4 shows the plasmid ppfl-MSN3H-Chol-cyt.

EXAMPLE 1

Cloning of the gene for cholesterol oxidase from Brevibacterium sterolicum

Brevibacterium sterolicum (BMTU 2407) is cultured in 500 ml nutrient broth (Difco) for 20 h at 30° C. The cells are harvested by centrifugation. The cell mass obtained in this way is resuspended in 20 mmol/l Tris/HCl pH 8.0 to 0.4 g cell wet weight/ml. 5 ml 24% (w/v) polyethylene glycol 6000, 2.5 ml 20 mmol/l Tris/HCl pH 8.0 and 10 mg lysozyme are added to 2.5 ml of this suspension and it is incubated for 14 h at 4° C. Then the cells are lysed by addition of 1 ml 20% (w/v) SDS and 2 mg protease K and incubation for 1 h at 37° C. An equal volume of 20 mmol/l Tris/HCl pH 8.0 is added to this solution and then 1 g CsCl and 0.8 g ethidium bromide are added per ml. This solution is separated by ultracentrifugation for 24 h at 40,000 rpm in a TV850 vertical rotor (DuPont). The DNA band is then withdrawn with an injection syringe. The removal of ethidium bromide and ethanol precipitation of the DNA is carried out as described in Sambrook et al., Molecular Cloning, A Laboratory Manual (1989).

7 µg of the DNA obtained in this manner is partially cleaved with the restriction endonuclease NlaIII (New England Biolab), separated electrophoretically on a 0.8% agarose gel and a size region of ca. 2–12 kb is cut out. The DNA fragments are isolated from the gel, cleaved with SphI and subsequently ligated into a plasmid vector pUC19 treated with alkaline phosphatase from calf intestine. This ligation preparation is transformed in competent E. coli K12 XL1-blue (Stratagene, Catalogue No. 200268). The transformed cells are plated on agar plates with LB medium containing 100 µg/ml ampicillin and incubated overnight at 37° C. The fully grown colonies are transferred onto nitrocellulose filters (Schleicher and Schull), lysed by treatment with toluene/chloroform vapour and the colony side of the filter is transferred onto indicator plates (see below). Cholesterol oxidase activity is tested on these indicator plates by a 15- to 30-minute incubation at room temperature.

Clones which show a colour reaction are selected and isolated. As a control these *E. coli* clones are streaked onto an agar plate with LB medium containing 100 μg/ml ampicillin, incubated overnight at 37° C., for verification the colonies that have grown on are again transferred onto two different nitrocellulose filters and lysed as described above with toluene/chloroform vapour. A filter is again placed on one of the indicator plates described above and the other filter is placed on an indicator plate without cholesterol. A positive colour reaction was only seen on the complete indicator plates containing the substrate cholesterol. This therefore demonstrates that the colour reaction caused by the corresponding *E. coli* clone is in fact due to active cholesterol oxidase.

Preparation of the indicator plates:

For the plate test to determine cholesterol oxidase activity, 100 ml 2% low-melting-point agarose (Sea Plaque BIOzym 50113) is melted and a solution of:

48 mg 4-aminoantipyrine (Boehringer Mannheim GmbH, Catalogue No. 073474)

306 mg EST (N-ethyl-N-sulfoethyl-3-methylaniline potassium salt (Boehringer Mannheim GmbH, Catalogue No. 586854))

2.5 mg horseradish peroxidase, degree of purity II (ca. 260 U/mg (Boehringer Mannheim GmbH, Catalogue No. 005096))

60 μl sodium azide solution (20%)

10 ml 1 mol/l potassium phosphate pH 7.2

150 mg cholic acid sodium salt (Merck, Catalogue No. 12448)

10 ml cholesterol substrate solution (see below)

$H_2O$ to a volume of 100 ml pre-warmed to a temperature of 42° C. is added to the melted agarose, carefully mixed, 10 ml portions are poured into Petri dishes and kept in the dark for storage.

Cholesterol substrate solution:

500 mg cholesterol (Boehringer Mannheim GmbH, Catalogue No. 121312) is dissolved in 12.5 ml 1-propanol (Merck, Catalogue No. 997), mixed well after addition of 10 g Thesit (Boehringer Mannheim GmbH, Catalogue No. 006190) and water is added to a volume of 100 ml. The substrate solution can be stored for several months at room temperature.

EXAMPLE 2

Characterization of the cholesterol oxidase gene

The plasmid of a clone obtained according to example 1 (pUC-chol-B2) is isolated according to standard methods and subjected to restriction mapping using the restriction endonucleases BamHI, EcoRI, KpnI, XhoI, PstI. It turns out that a DNA fragment from the genome of Brevibacterium with a size of ca. 5.5 kb is inserted into the plasmid pUC-Chol-B2. By subcloning various partial fragments of this 5.5 kb piece and subsequently determining the cholesterol oxidase activity of the *E. coli* clones obtained, it is possible to narrow down the cholesterol oxidase gene to a BamHI fragment of 2.3 kb size. The plasmid with this fragment is denoted pUC-Chol-B2-BB (FIG. 1). The DNA sequence of this fragment is determined and examined for a reading frame which codes for cholesterol oxidase. The sequence of this reading frame for mature cholesterol oxidase is given in SEQ ID NO 1.

EXAMPLE 3

Construction of a plasmid for expressing the cholesterol oxidase gene with a heterologous signal sequence Comparison of the N-terminal amino acid sequence of cholesterol oxidase which was isolated from Brevibacterium with the entire reading frame coding for cholesterol oxidase from pUC-Chol-B2-BB shows that the first 52 coded amino acids of the gene sequence are absent in the mature protein. These 52 amino acids have the structure of a typical export signal sequence of gram-positive prokaryotes (von Heijne, Biochim. Biophys.

Acta 947 (1988), 307–333). In order to construct recombinant cholesterol oxidase genes in which this signal sequence is replaced by other sequences, a 387 bp DNA fragment from the plasmid pUC-Chol-B2-BB is firstly amplified by means of PCR using the oligonucleotides shown in SEQ ID NOS 30 and 31. This fragment contains the region coding for the N-terminal part of the mature oxidase with a new SphI cleavage site directly in front of the N-terminus of the amino acid sequence of the mature enzyme. This PCR fragment is cleaved with SphI and PstI and ligated together with a PstI EcoRI fragment from pUC-Chol-B2-BB which contains the remaining part of the cholesterol oxidase gene into the expression vector pmglsphI cleaved with SphI and EcoRI and in this way the vector pmgl-Chol-SB is obtained. In this vector the cholesterol oxidase gene contains a signal sequence from *Salmonella typhimurium* that is functional in *E. coli* (described in WO 88/093773).

EXAMPLE 4

Construction of a plasmid for expression of the cholesterol oxidase gene without a signal peptide-coding sequence under the control of the lacUV5 promoter A DNA fragment of ca. 1.85 kb in size which contains the entire part of the coding sequence of mature cholesterol oxidase but not the sequence coding for the signal peptide is cut out of the plasmid pmgl-Chol-SB by treatment with the restriction endonucleases SphI and BamHI. This fragment is inserted into the plasmid vector pUC19 which has previously been cleaved with SphI and BamHI. In the plasmid plac-Chol-cyt obtained in this manner the cholesterol oxidase gene is present in the correct reading frame and is fused to the first ten codons of the lacZ' gene from pUC19 and is under the control of the lacUV5 promoter (FIG. 2).

EXAMPLE 5

Construction of a plasmid for the expression of the cholesterol oxidase gene without a signal peptide-coding sequence under the control of the oxygen-regulated pfl promoter A DNA fragment of 432 bp in size which contains a ClaI cleavage site in front of the ATG start codon is produced from the plasmid plac-Chol-cyt by the PCR technique using the oligonucleotides shown in SEQ ID NOS 32 and 33. This PCR fragment is cut with ClaI and PstI. In addition a fragment with the remaining C-terminal part of the cholesterol oxidase gene is cleaved from the plasmid plac-Chol-cyt by treatment with the restriction endonucleases PstI and BamHI. Both fragments are simultaneously ligated into the expression vector pfl 20AT1-SD cleaved with BamHI and ClaI. The correct ligation product now contains the reading frame of mature cholesterol oxidase fused to the first ten codons of the lacZ' gene from pUC19 under the control of the oxygen-regulated pfl promoter (FIG. 3). This plasmid is denoted ppfl-Chol-cyt.

EXAMPLE 6

Construction of a plasmid for expressing the cholesterol oxidase gene with an alternative N-terminal fusion sequence In order to remove the SphI cleavage site of the plasmid ppfl-Chol-cyt located in the 3' untranslated region of the cholesterol oxidase gene, the plasmid DNA is cleaved with SmaI and EcoRV and again religated. 100 ng of the plasmid ppfl-Chol-cyt-Δterm formed in this manner is then cleaved with the restriction enzymes ClaI and SphI. The DNA fragment of 4.76 kb in size which is formed is electrophoretically separated in low-melting point agarose, cleaved and eluted (Glassmilk®-Kit, Bio 101). 100 ng of the DNA fragment purified in this manner is admixed with 50 pmol of an adapter oligonucleotide with the sequence shown in SEQ ID NO 34 (in which "N" denotes an equimolar mixture of all 4 bases) and treated for 2 hours at 37° C. with T4 DNA ligase. Subsequently the mixture is admixed with a mixture of 4 dNTP's (final concentration 0.125 mmol/l) and treated for 40 minutes at 37° C. with Klenow DNA polymerase. The plasmid DNA obtained in this manner is transformed in E. coli XL1-blue (Stratagene). Individual colonies of the clones obtained are compared with the aid of the colony activity test described in example 1 with regard to their cholesterol oxidase activity. Clones with a high cholesterol oxidase activity are isolated and the plasmid DNA is characterized by restriction analysis and DNA sequencing. The plasmid of a clone with a particularly high cholesterol oxidase activity was found to have the sequence SEQ ID NO 23. The plasmid concerned is denoted ppfl-MSM3H-Chol-cyt-Δterm. It is to be expected that further clones suitable for a particularly high expression may be found in the described manner after isolation and characterization of an adequate number of different clones. In order to complete again the 3' untranslated part, the plasmid ppfl-MSM3H-Chol-cyt-Δterm is cleaved with ClaI and XhoI. A DNA fragment of ca. 1.1 kb with the translation initiation region and the N-terminal part of the cholesterol oxidase gene is isolated and ligated into the plasmid ppfl-Chol-cyt which is also cleaved with ClaI and XhoI (FIG. 4). The plasmid obtained is denoted ppfl-MSN3H-Chol-cyt.

EXAMPLE 7

Comparison of the formation of cholesterol oxidase by the various expression plasmids in E. coli The plasmids pUC-Chol-B2, pUC-Chol-B2-BB, pmgl-Chol-SB, plac-Chol-cyt, pplf-Chol-cyt, ppfl-MSN3H-Chol-cyt are each transformed in E. coli K12 XL1-blue. In order to compare the amount of enzyme formed, the clones are each cultured for 15 hours at 30° C. in LB medium containing 200 μg/ml ampicillin and the following further additives:

clones containing the plasmids pUC-Chol-B2, pUC-Chol-B2-BB, plac-Chol-cyt in which the cholesterol oxidase gene is in each case under the control of the lacUV5 promoter are additionally receive 1 mmol/l IPTG, the clone containing the plasmid pmgl-Chol-SB with the glucose-repressed mgl promoter receives no further additives, clones containing the plasmids ppfl-Chol-cyt, ppfl-MSN3H-Chol-cyt with the oxygen-regulated pfl promoter recieve 0.4% glucose and are grown in closed serum flasks that have been gassed with nitrogen in which the medium was adjusted with KOH to pH 7.0. After the culture is completed the cell density achieved is determined by photometric measurement of the turbidity at 420 nm. The cells of 1 ml culture broth are then sedimented by centrifugation in a microcentrifuge at 10,000 g and again resuspended in 0.5 ml redistilled $H_2O$. The cell rupture is carried out by 2×30 seconds ultrasonic treatment (Branson Sonifier, model 450, standard microtip, conical). The cell extracts obtained in this manner are used in the following enzyme test after appropriate dilution: for this the following are pipetted into quartz cuvettes:

3 ml potassium phosphate buffer (0.5 mol/l, pH 7.5) containing 0.4% Thesit® (Boehringer Mannheim GmbH, Catalogue No. 006190), 0.1 ml cholesterol solution (0.4% cholesterol, 10% 1-propanol, 10% Thesit®), 0.02 ml $H_2O_2$ (0.49 mol/l in redistilled water), it is mixed, after addition of 0.02 ml catalase (from bovine liver, 20 mg protein/ml, specific activity ca. 65,000 U/mg, Boehringer Mannheim GmbH, Catalogue No. 0156744 diluted immediately to 0.075–0.15 U/ml before measurement with ice-cold potassium phosphate buffer, containing 0.4% Thesit) it is again mixed, the solution is brought to a temperature of 25° C. and subsequently the reaction is started by addition of 0.05 ml sample solution. After careful mixing the change in absorbance at 240 nm is monitored and the activity of cholesterol oxidase is determined from the linear region of the absorbance curve:

$$\text{Actvity} = \frac{3.19}{\in 240 \times 0.05 \times 1} \Delta A \min.(U/\text{ml sample solution})$$

in which $\in 240 = 15.5 \text{ mmol}^{-1} \times 1 \times \text{cm}^{-1}$.

The values obtained for cell density and enzyme activity are shown in Table 1.

TABLE 1

| Clone/plasmid | Cell density (A 420) | Units per cell density | Units per ml |
|---|---|---|---|
| pUC-chol-B2 | 7.0 | 0.007 | 0.049 |
| pUC-chol-B2-BB | 8.4 | 0.068 | 0.571 |
| pmgl-chol-SB | 1.3 | 0.014 | 0.018 |
| plac-chol-cyt | 8.6 | 0.725 | 6.235 |
| ppfl-chol-cyt | 1.25 | 1.675 | 2.094 |
| ppfl-MSN3H-chol-cyt | 3.7 | 1.463 | 5.413 |

The results obtained show that using such constructs which cause a cytoplasmic expression of cholesterol oxidase, a considerably higher activity of the recombinantly produced cholesterol oxidase can be obtained than with those constructs which lead to a secretion of the recombinantly produced cholesterol oxidase.

I claim:

1. A purified peptide cholesterol oxidase, comprising the amino acid sequence shown in SEQ ID NO:2, wherein said peptide does not include a *B. sterolicum* signal sequence.

2. Recombinant cholesterol oxidase comprising an N-terminal sequence selected from the group consisting of the sequences shown in SEQ ID NO 7, 9, 11, 13, 15 and 17.

3. Recombinant cholesterol oxidase of claim 2 comprising a sequence selected from the group consisting of the sequences shown in SEQ ID NO 19, 21, 23, 25, 27 or 29.

4. A DNA molecule, which codes for a peptide with cholesterol oxidase activity or a sequence which is complementary thereto and which is selected from the group consisting of:

a) the DNA sequence shown in SEQ ID NO 1 or a DNA sequence which is complementary thereto, b) DNA sequences which hybridize with the DNA sequence shown in SEQ ID NO 1, and c) DNA sequences which code for a peptide with the same amino acid sequence as the amino acid sequences coded by the DNA sequences of a) and b),
      wherein said peptide is obtainable from B. sterolicum and can be expressed in an enzymatically active form in *E. coli* and wherein said DNA does not encode a *B. sterolicum* signal sequence.

5. The DNA of claim 4, comprising a 5' sequence selected from the group consisting of the sequences shown in SEQ ID NO 6, 8, 10, 12, 14 and 16.

6. The DNA of claim 4, comprising a sequence selected from the group consisting of the sequences shown in SEQ ID NO 18, 20, 22, 24, 26 and 28.

7. The DNA of claim 4, comprising the sequence shown in SEQ ID NO 1.

8. A process for the production of a recombinant cholesterol oxidase comprising:

a) transforming a host cell with an expression vector comprising the DNA of claim 4, b) culturing the transformed host cells, and c) isolating the cholesterol oxidase formed from the cytoplasm of the transformed cells.

9. The process of claim 8, wherein the DNA comprises a 5' sequence selected from the group consisting of the sequences shown in SEQ ID NO 6, 8, 10, 12, 14 and 16.

10. The process of claim 8, wherein the DNA comprises a sequence selected from the group consisting of the sequences shown in SEQ ID NO 18, 20, 22, 24, 26, and 28.

11. A method for the determination of cholesterol comprising combining the recombinant cholesterol oxidase according to claim 3 with a cholesterol containing sample under conditions suitable for the oxidation of cholesterol to cholesten-3-one and $H_{22}$. and determining cholesterol-based on the presence of cholesten-3-one and $_2O_2$.

12. A purified peptide cholesterol oxidase, consisting of the amino acid sequence shown in SEQ ID NO:2.

* * * * *